US012685562B2

(12) United States Patent
Gono et al.

(10) Patent No.: US 12,685,562 B2
(45) Date of Patent: Jul. 21, 2026

(54) CANNULATION METHOD, INFORMATION PROCESSING SYSTEM AND MEDICAL SYSTEM

(71) Applicant: OLYMPUS CORPORATION, Tokyo (JP)

(72) Inventors: Kazuhiro Gono, Sagamihara (JP); Hiromi Sanuki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 469 days.

(21) Appl. No.: 17/989,186

(22) Filed: Nov. 17, 2022

(65) Prior Publication Data

US 2023/0149043 A1     May 18, 2023

Related U.S. Application Data

(60) Provisional application No. 63/294,597, filed on Dec. 29, 2021, provisional application No. 63/280,716, filed on Nov. 18, 2021.

(51) Int. Cl.
*A61B 17/34* (2006.01)
*A61B 1/00* (2006.01)
(Continued)

(52) U.S. Cl.
CPC .... *A61B 17/3478* (2013.01); *A61B 1/000096* (2022.02); *A61B 1/015* (2013.01);
(Continued)

(58) Field of Classification Search
CPC .......... A61B 17/3478; A61B 1/000096; A61B 1/015; A61B 1/2736; A61B 2017/00818;
(Continued)

(56) References Cited

U.S. PATENT DOCUMENTS

| 7,953,612 B1 | 5/2011 | Palmese et al. |
| 11,801,114 B2 | 10/2023 | Lang |

(Continued)

FOREIGN PATENT DOCUMENTS

| JP | H11-019027 A | 1/1999 |
| JP | 2003-038419 A | 2/2003 |

(Continued)

OTHER PUBLICATIONS

Yi et al., "Quantitative Analysis of Colonoscopy Skills Using the KAIST-Ewha Colonoscopy Simulator II", Frontier in the Convergence of Bioscience and Information Technologies 2007, Year: 2007.

(Continued)

*Primary Examiner* — Courtney B Fredrickson
*Assistant Examiner* — Anna E Vargas
(74) *Attorney, Agent, or Firm* — Scully, Scott, Murphy & Presser, P.C.

(57)     ABSTRACT

A cannulation method includes inserting an endoscope into a duodenum, bringing a distal end section of the endoscope to a position where a duodenal papilla is within a field of view of the endoscope, promoting secretion of pancreatic juice or bile by administering a drainage stimulant, determining an amount of relaxation of the duodenal papilla, and performing cannulation into a biliary duct through the duodenal papilla where the amount of relaxation is greater than a predetermined amount.

10 Claims, 27 Drawing Sheets

(51) Int. Cl.

| | |
|---|---|
| *A61B 1/015* | (2006.01) |
| *A61B 1/273* | (2006.01) |
| *A61B 17/00* | (2006.01) |

(52) U.S. Cl.

CPC .. *A61B 1/2736* (2013.01); *A61B 2017/00818* (2013.01); *A61B 2017/00893* (2013.01)

(58) Field of Classification Search

CPC ........... A61B 2017/00893; A61B 5/42; A61B 5/4222; A61B 5/4244; A61B 5/425; A61B 10/0045; A61B 2010/0061

See application file for complete search history.

(56) References Cited

U.S. PATENT DOCUMENTS

| | | | |
|---|---|---|---|
| 12,048,413 | B2 | 7/2024 | Tada et al. |
| 12,290,414 | B2 | 5/2025 | Lang |
| 12,478,433 | B2 | 11/2025 | Mino et al. |
| 2003/0078473 | A1 | 4/2003 | Richardson |
| 2004/0015329 | A1 | 1/2004 | Shayegan et al. |
| 2007/0038080 | A1 | 2/2007 | Salisbury, Jr. et al. |
| 2007/0185377 | A1 | 8/2007 | Murakami et al. |
| 2008/0058425 | A1* | 3/2008 | Hurley .................... A61P 21/02 |
| | | | 514/645 |
| 2008/0214890 | A1 | 9/2008 | Motai et al. |
| 2008/0249356 | A1 | 10/2008 | Motai et al. |
| 2008/0249358 | A1 | 10/2008 | Motai et al. |
| 2010/0041949 | A1 | 2/2010 | Tolkowsky |
| 2010/0056910 | A1 | 3/2010 | Yanuma |
| 2010/0134605 | A1 | 6/2010 | Demos et al. |
| 2014/0212849 | A1 | 7/2014 | Naiwala et al. |
| 2014/0303435 | A1 | 10/2014 | Taniguchi |
| 2015/0164608 | A1 | 6/2015 | Bartenstein |
| 2015/0265807 | A1 | 9/2015 | Park et al. |
| 2016/0206227 | A1 | 7/2016 | Marashdeh et al. |
| 2016/0206228 | A1 | 7/2016 | Angulo et al. |
| 2016/0338716 | A1 | 11/2016 | Aslinia et al. |
| 2016/0353970 | A1 | 12/2016 | Inoue |
| 2017/0086929 | A1 | 3/2017 | Moll et al. |
| 2018/0040126 | A1 | 2/2018 | Bayer |
| 2018/0296281 | A1 | 10/2018 | Yeung et al. |
| 2019/0029757 | A1 | 1/2019 | Roh et al. |
| 2019/0208990 | A1 | 7/2019 | Chelala et al. |
| 2019/0340956 | A1 | 11/2019 | Lindkvist et al. |
| 2020/0030575 | A1* | 1/2020 | Bogusky ........... A61M 16/0488 |
| 2020/0178773 | A1 | 6/2020 | Miller |
| 2020/0281449 | A1 | 9/2020 | Yoshimura |
| 2021/0137634 | A1 | 5/2021 | Lang |
| 2021/0153808 | A1 | 5/2021 | Tada et al. |
| 2021/0196398 | A1 | 7/2021 | Ye et al. |
| 2022/0192466 | A1 | 6/2022 | Nishimura |
| 2023/0123739 | A1 | 4/2023 | Mino et al. |
| 2023/0148847 | A1 | 5/2023 | Gono et al. |
| 2023/0148848 | A1 | 5/2023 | Gono et al. |
| 2023/0148849 | A1 | 5/2023 | Inoue et al. |
| 2023/0153288 | A1 | 5/2023 | Gono |
| 2023/0157768 | A1 | 5/2023 | Meguro |
| 2023/0200682 | A1 | 6/2023 | Yoshioka et al. |
| 2024/0016551 | A1 | 1/2024 | Duval et al. |
| 2024/0197163 | A1 | 6/2024 | Inoue et al. |
| 2024/0252775 | A1 | 8/2024 | Gage et al. |
| 2025/0017689 | A1 | 1/2025 | Lang |
| 2025/0064296 | A1* | 2/2025 | Sokolov ................. A61B 90/39 |

FOREIGN PATENT DOCUMENTS

| | | | |
|---|---|---|---|
| JP | 2005-334474 A | 12/2005 | |
| JP | 2008-253780 A | 10/2008 | |
| JP | 2011-240152 A | 12/2011 | |
| JP | 2012-213436 A | 11/2012 | |
| JP | 2013-069251 A | 4/2013 | |
| JP | 2019-197436 A | 11/2019 | |
| WO | WO-2006042186 A2 * | 4/2006 | .............. A61P 41/00 |
| WO | 2021/049475 A1 | 3/2021 | |

OTHER PUBLICATIONS

U.S. Office Action dated Dec. 18, 2023 received in U.S. Appl. No. 17/989,160.

Japanese Office Action dated Mar. 5, 2024 received in 2022-171250.

U.S. Office Action dated Apr. 8, 2025 received in U.S. Appl. No. 17/989,126.

Japanese Office Action dated Oct. 3, 2023 received in 2022-171250.

Extended European Search Report dated Apr. 5, 2023 received in 22207769.5.

U.S. Office Action dated Apr. 18, 2025 received in U.S. Appl. No. 17/989,146.

U.S. Final Office Action dated Oct. 15, 2025 received in U.S. Appl. No. 17/989,146.

U.S. Office Action dated Aug. 26, 2025 received in U.S. Appl. No. 17/989,108.

US Office Action dated Feb. 25, 2026 received in U.S. Appl. No. 18/612,092.

US Office Action dated Mar. 26, 2026 received in U.S. Appl. No. 17/989,146.

US Office Action dated Apr. 8, 2026 received in U.S. Appl. No. 17/989,126.

* cited by examiner

ESOPHAGUS

LIVER

GALLBLADDER

INSERTION SECTION
OF ENDOSCOPE

BILIARY DUCT

DUODENUM

PANCREAS

DISTAL END OF
ENDOSCOPE

PAPILLARY PORTION

PANCREATIC DUCT

FIG.4

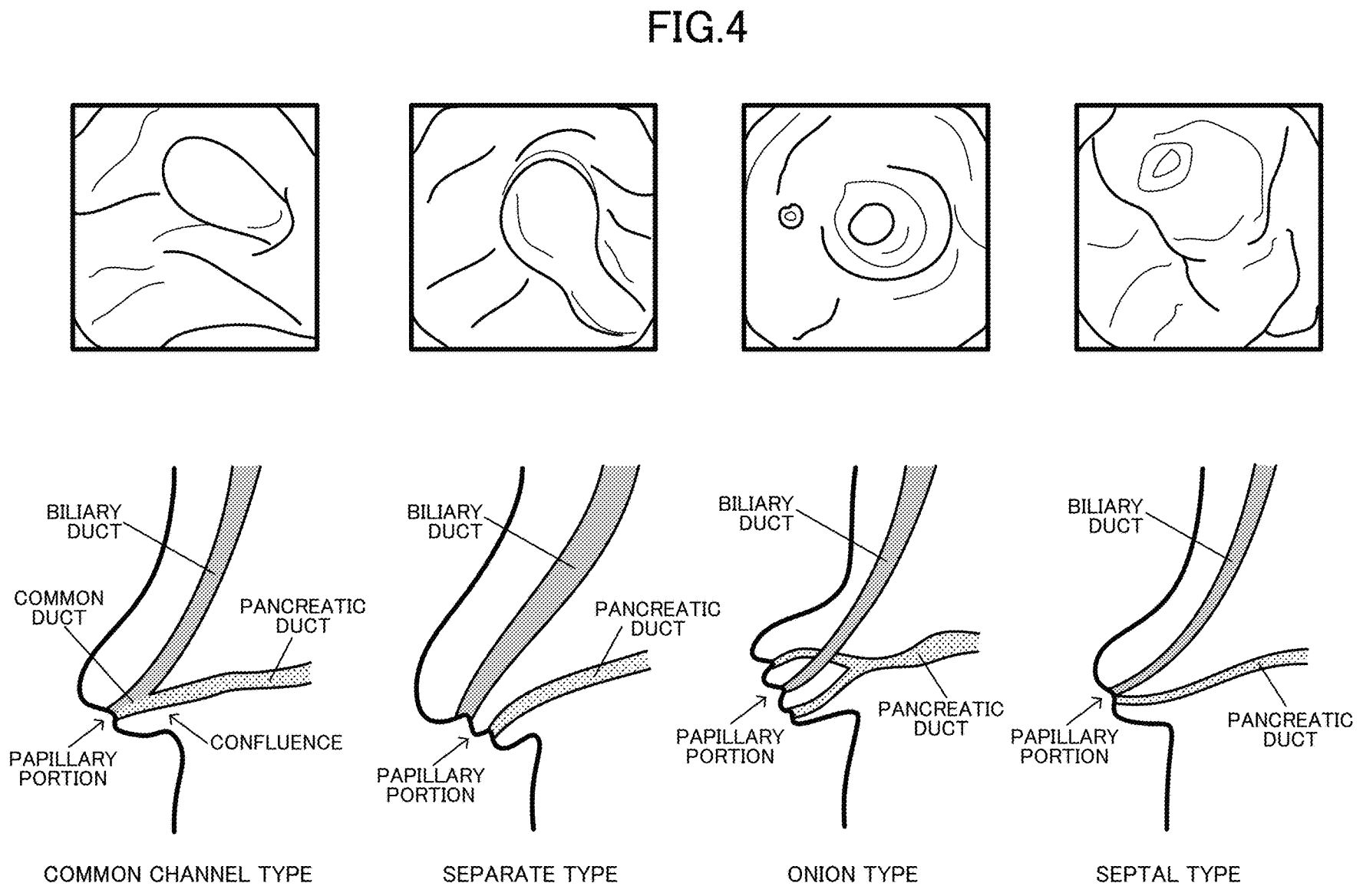

SEPTAL TYPE

BILIARY DUCT

PANCREATIC DUCT

PAPILLARY PORTION

ONION TYPE

BILIARY DUCT

PANCREATIC DUCT

PAPILLARY PORTION

SEPARATE TYPE

BILIARY DUCT

PANCREATIC DUCT

PAPILLARY PORTION

COMMON CHANNEL TYPE

BILIARY DUCT

COMMON DUCT

PANCREATIC DUCT

CONFLUENCE

PAPILLARY PORTION

UNRELAXED STATE

RELAXED STATE

FIG.13

CANNULATION METHOD, INFORMATION PROCESSING SYSTEM AND MEDICAL SYSTEM

CROSS-REFERENCE TO RELATED APPLICATIONS

This application claims the benefit of priority to U.S. Provisional Application Nos. 63/280,716 filed Nov. 18, 2021, and 63/294,597 filed Dec. 29, 2021, the entire contents of which is incorporated herein by reference.

BACKGROUND

A technique called endoscopic retrograde cholangiopancreatography (ERCP) has been known that captures an X-ray image or a CT image of biliary duct by inserting a cannula into a biliary duct from a treatment tool channel of an endoscope, injecting a contrast agent from the cannula, and performing X-ray imaging or CT imaging. U.S. Patent Application Publication No. 2010/0056910 discloses a procedure to approach a biliary duct using a flexible guide wire in order to allow for easy insertion without inhibiting drainage of pancreatic juice.

SUMMARY

An aspect of the present disclosure relates to a cannulation method includes: inserting an endoscope into a duodenum, bringing a distal end section of the endoscope to a position where a duodenal papilla is within a field of view of the endoscope, promoting secretion of pancreatic juice or bile by administering a drainage stimulant, determining an amount of relaxation of the duodenal papilla, and performing cannulation into a biliary duct through the duodenal papilla where the amount of relaxation is greater than a predetermined amount.

Another aspect of the present disclosure relates to an information processing system includes a processor comprising hardware. The processor is configured to acquire an endoscope image from an endoscope, the endoscope image showing a duodenal papilla, determine an amount of relaxation of the duodenal papilla based on the acquired endoscope image, and determine whether or not to administer a drainage stimulant promoting secretion of pancreatic juice or bile based on the determined amount of relaxation.

Still another aspect of the present disclosure relates to a medical system including: an information processing system described above; and the endoscope.

BRIEF DESCRIPTION OF THE DRAWINGS

FIG. 4 shows classification types of biliary and pancreatic ducts corresponding to endoscope images of the papillary portion.

FIG. 13 explains a process using a trained model.

DESCRIPTION OF EXEMPLARY EMBODIMENTS

Figure 1:
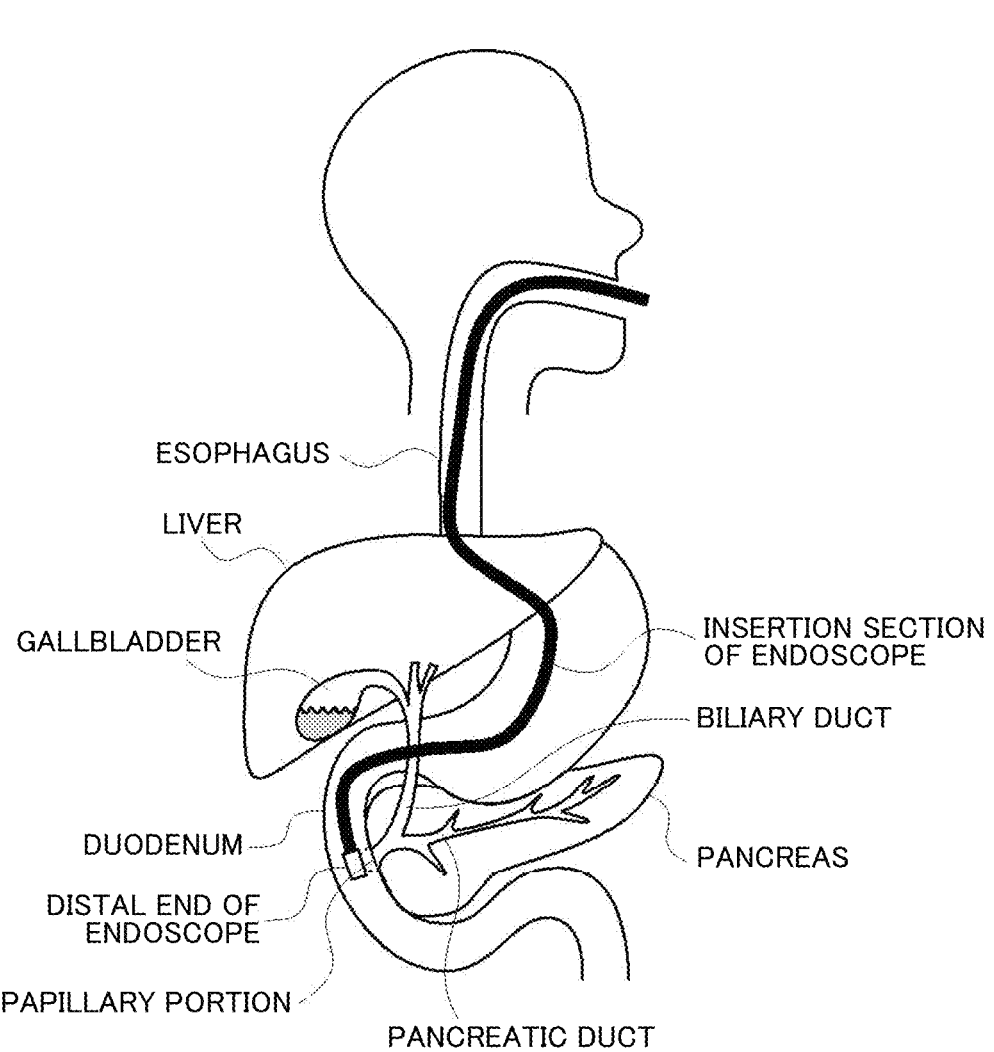
FIG. 1 shows organs and tissues involved in the ERCP procedure.

The following disclosure provides many different embodiments, or examples, for implementing different features of the provided subject matter. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Explanation of ERCP

The present embodiment relates to a cannulation method and an information processing system for performing ERCP and the like. ERCP stands for Endoscopic Retrograde Cholangiopancreatography. First, before describing the present embodiment, the details of procedure of ERCP is described below.

FIG. 1 shows organs and tissues involved in the ERCP procedure. The organs include a multiple types of tissues, forming a unique structure with a specific function. In FIG. 1, the liver, gallbladder, pancreas, esophagus, stomach, and duodenum are shown as organs. Tissues are formed by related cells combined, and examples include blood vessels, muscles, skin, and the like. In FIG. 1, a biliary duct and a pancreatic duct are shown as tissues.

The biliary duct is the target of the ERCP procedure. The biliary duct is a pipeline for allowing the bile produced in the liver to flow into the duodenum. When approaching the biliary duct using an endoscope, a treatment tool inserted into the channel of the endoscope is inserted to the biliary duct from the papillary portion of the duodenum while holding the endoscope at the position of the duodenum. Hereinafter, the papillary portion of the duodenum is simply referred to as a papillary portion. The papillary portion is a region including an opening of the luminal tissue with respect to the duodenum. Not only the opening but also the structure around the opening is referred to as a papillary portion. The opening of the luminal tissue is the opening of a common duct with respect to the duodenum. The common duct is formed as the confluence of the biliary duct and pancreatic duct. However, as described later, the papillary portion largely varies between individuals. For example, in some cases, the biliary duct opens directly to the duodenum without being merged with the pancreatic duct. In this case, the opening of the luminal tissue is the opening of the biliary duct.

Figure 2:
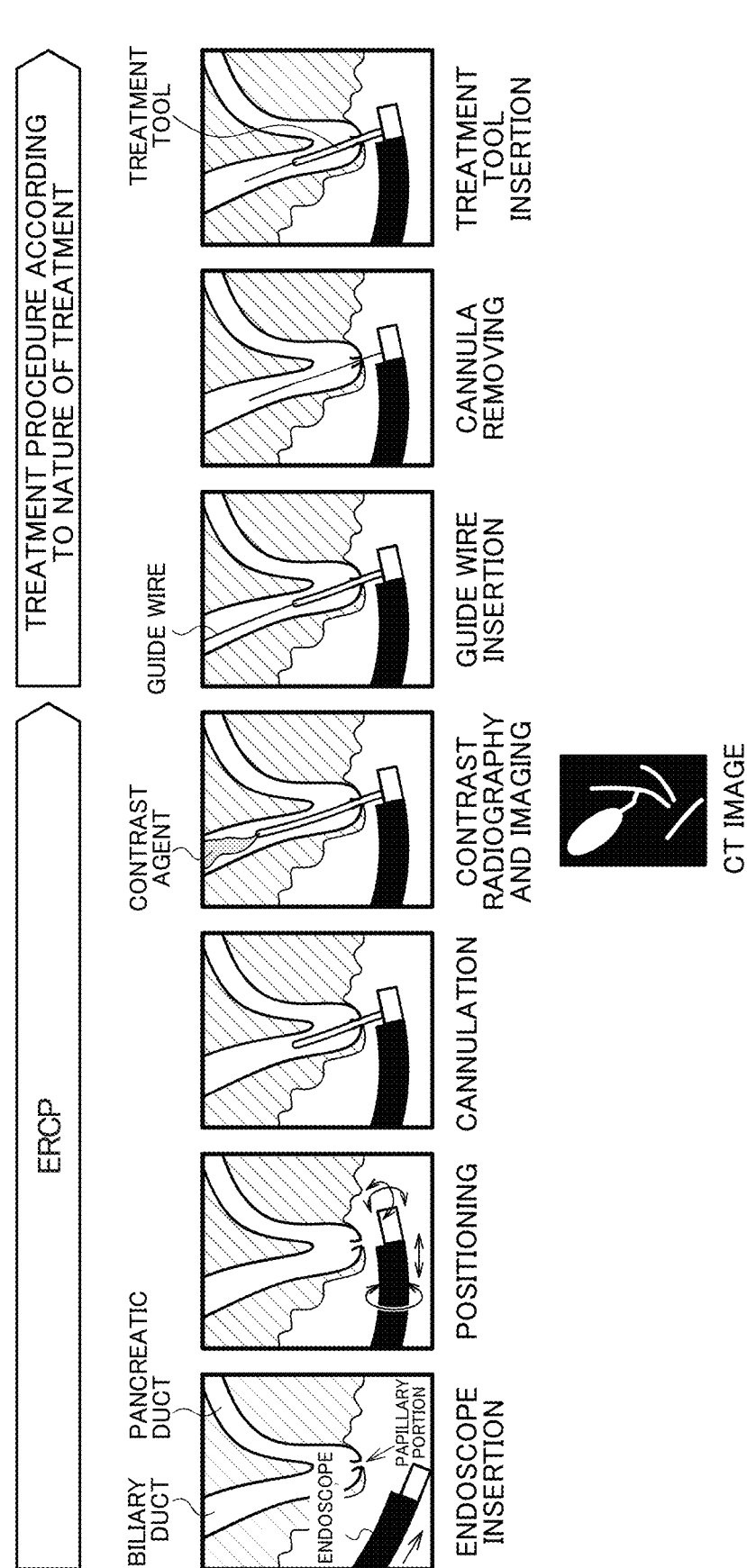
FIG. 2 shows a flow of the ERCP procedure.

FIG. 2 shows a flow of the ERCP procedure. In ERCP, a side-viewing type endoscope in which a camera, an illumination lens, and an opening of a treatment tool channel are provided on a side surface of a distal end section of the endoscope is used. The camera is also referred to as an imaging device.

In the endoscope insertion step, the insertion section of the endoscope is inserted from the mouth to the duodenum through the esophagus and stomach. At this time, the insertion section is inserted until the papillary portion becomes roughly visible in the field of view of the endoscope. Next, in the positioning step, the position of the endoscope is adjusted relative to the papillary portion. Specifically, the position of the distal end section of the endoscope is adjusted so that the papillary portion is within the imaging range of the camera of the endoscope. Alternatively, the position of the distal end section of the endoscope is adjusted so that the camera of the endoscope is facing directly front of the papillary portion and the papillary portion appears in the center of the field of view.

Then, in the cannulation step, a cannula is inserted from the papillary portion into the biliary duct. Specifically, the cannula is inserted into the treatment tool channel of the endoscope so that the cannula protrudes from the channel opening of the distal end section of the endoscope. The distal end of the cannula is inserted into the common duct from the opening of the common duct, and the cannula is further inserted through the confluence of the biliary duct and the pancreatic duct toward the direction of the biliary duct. Cannulation refers to insertion of a cannula into a body. A cannula is a medical tube that is inserted into a body for medical purposes.

Next, in the contrast radiography and imaging step, a contrast agent is injected into the cannula and poured into the biliary duct through the distal end of the cannula. By performing X-ray or CT imaging in this state, an X-ray image or a CT (Computed Tomography) image showing the biliary duct, gallbladder, and pancreatic duct can be obtained. The procedure of ERCP has been described. After the procedure, various treatments are performed according to the results of diagnosis based on the X-ray image or CT image. An example of the treatment is described below.

In a guide wire insertion step, a guide wire is inserted into a cannula so that the guide wire is protruded from the distal end of the cannula, and the guide wire is inserted into the biliary duct. In a cannula removing step, the cannula is removed while leaving the guide wire inside the biliary duct. As a result, only the guide wire protrudes from the distal end section of the endoscope, indwelling in the biliary duct. Next, in a treatment tool insertion step, the treatment tool is inserted into the biliary duct along the guide wire. An example of a treatment tool is a basket or stent. The basket is used with a catheter. While allowing the guide wire to pass through the catheter, the catheter is inserted into the biliary duct along the guide wire. A basket made of a plurality of metal wires is inserted into the biliary duct from the distal end of the catheter, an object to be removed, such as a gallstone, is placed in the basket and held, and the object to be removed is taken out from the biliary duct by removing the basket and catheter in this state from the biliary duct. A stent is also used in a similar manner with a catheter and inserted into the biliary duct from the distal end of the catheter. The narrow portion of the biliary duct can be widened by inserting a stent; further, by keeping the stent therein, the narrow portion is held in a widened state by the indwelling stent.

Figure 3:
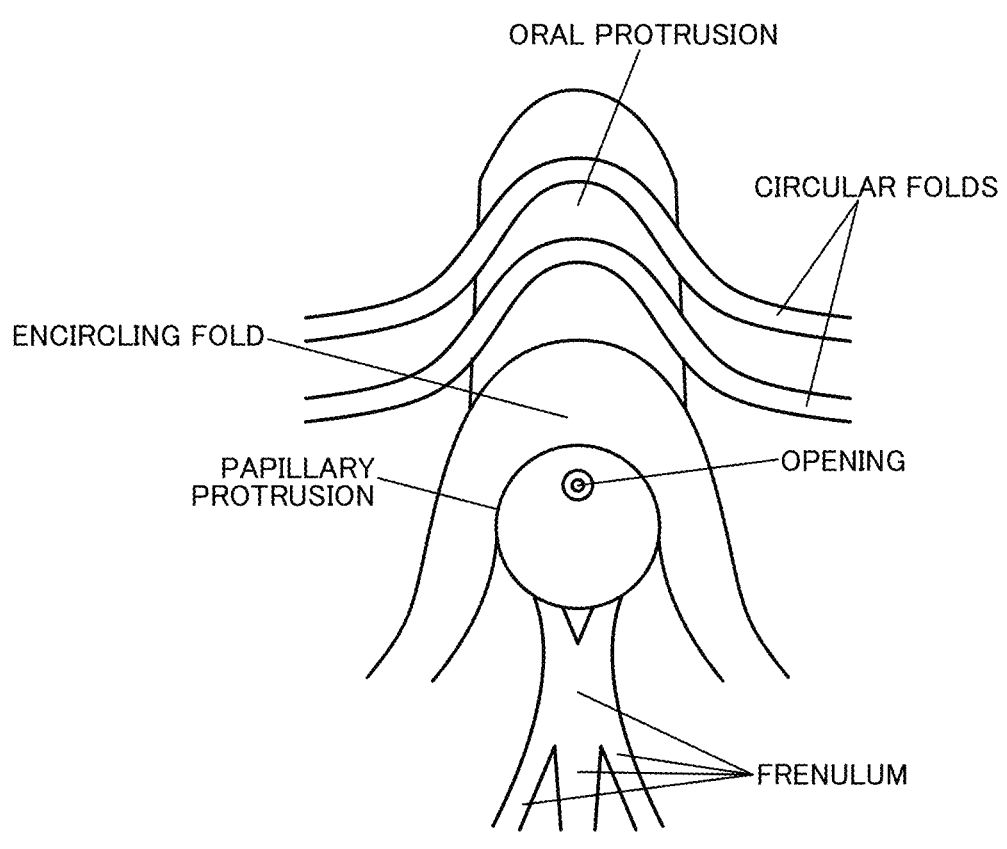
FIG. 3 shows a schematic diagram of the form of papillary portion viewed directly from the front.

The ERCP procedure is performed as described above. The cannulation step of inserting the cannula has the following challenges. For example, FIG. 3 is a schematic diagram of the form of the papillary portion viewed directly from the front. As shown in FIG. 3, unique structures exist around the opening of the papillary portion. Specifically, structures respectively called a frenulum, a papillary protrusion, an encircling fold, circular folds, and an oral protrusion are present around the opening, which is a major papilla. As shown in FIG. 3, the opening of the papillary portion is usually closed. In some cases, the opening is tight closed, making it impossible to insert the cannula smoothly. The opening into which the cannula cannot be inserted is incised using a procedure called endoscopic spincterotomy (EST) and cannulated.

Additionally, the shapes of the opening and its surroundings in the papillary portion differ from individual to individual. For example, FIG. 4 shows classification patterns for the papillary portion and examples of endoscope images observed in the respective classification patterns. As shown in FIG. 4, the classification patterns based on the paths of the biliary and pancreatic ducts include, for example, a common channel type, a separate type, an onion type, and a septal type. The classification patterns based on the opening of the papillary portion include a separate opening type, an onion type, a nodular type, a villous type, a flat type, and a vertically elongated type.

As such, the opening of the papillary portion is usually closed and the shapes of the opening and its surroundings differ from individual to individual, so that the cannulation step involves difficulty in smoothly inserting the cannula. In this regard, U.S. Patent Application Publication No. 2010/0056910 mentioned above discloses a procedure that allows for easy insertion without inhibiting drainage of pancreatic juice by approaching the biliary duct using a flexible guide wire. However, the publication does not suggest any procedure that facilitates insertion of the cannula into the opening prior to insertion of the cannula.

Cannulation Method

Hence, in the present embodiment, a drainage stimulant is administered to promote secretion of pancreatic juice or bile in a step prior to the cannulation. For example, prior to insertion of the cannula, an agent that promotes pancreatic juice, such as secretin, is sprayed to the papillary portion as a drainage stimulant. Alternatively, prior to insertion of the endoscope, a drainage stimulant may be administered orally. Such a step of promoting the secretion of pancreatic juice or bile by administration of the drainage stimulant can accelerate the secretion of pancreatic juice or bile to thereby loosen the region around the papillary portion and expand the opening. Specifically, the sphincter of Oddi in the papillary portion is relaxed, which widens the opening and facilitates insertion of the cannula into the opening. This allows even inexperienced operators or the like to easily insert the cannula into the opening of the papillary portion, facilitating an easier ERCP procedure.

Figure 5:
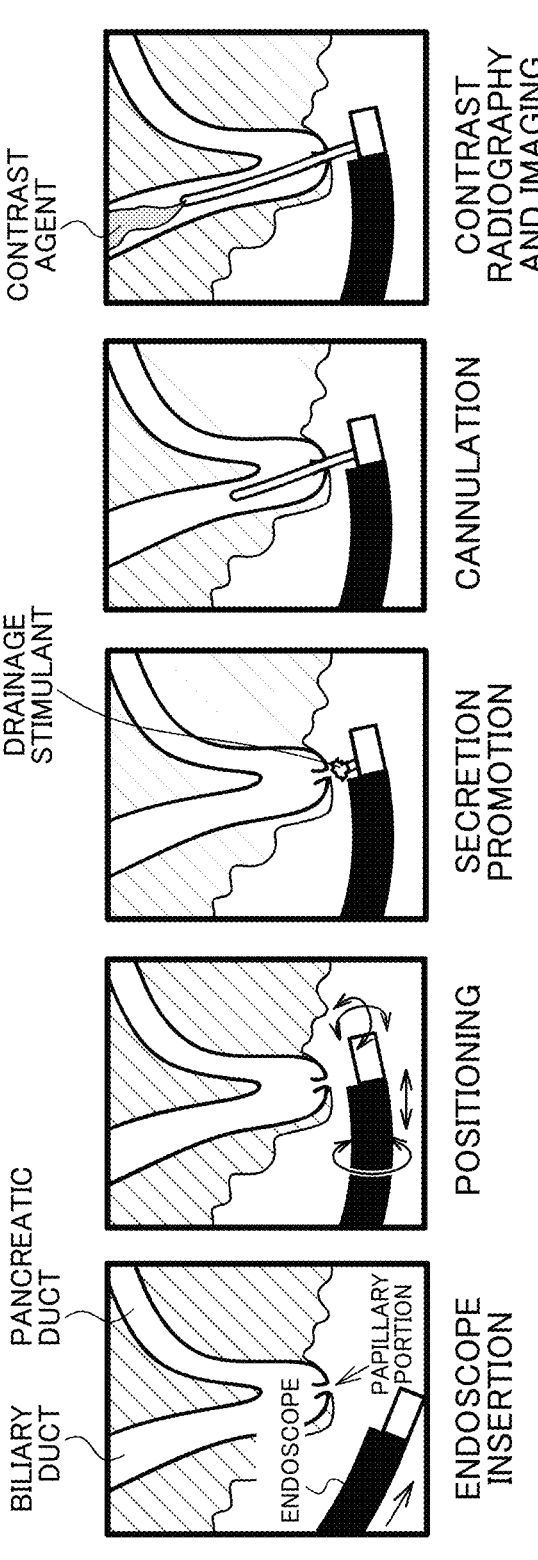
FIG. 5 explains a cannulation method of the present embodiment.
Figure 6:
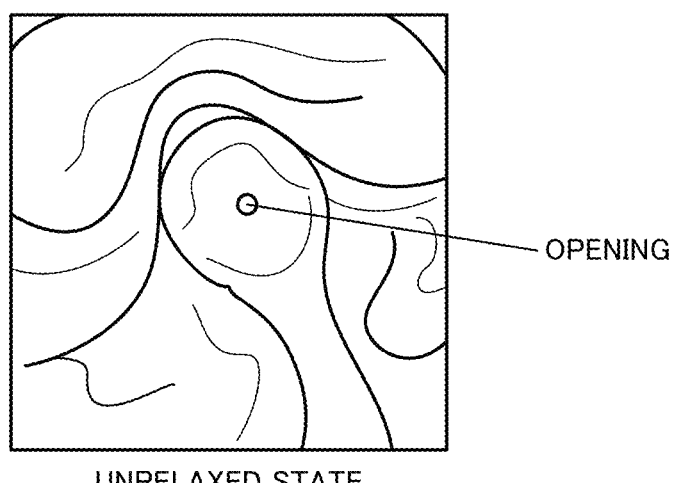
FIG. 6 schematically shows a relaxed state and an unrelaxed state of the papillary portion.
Figure 6:
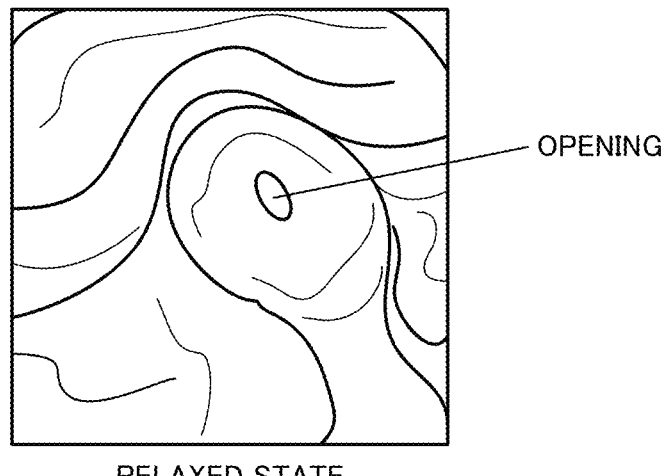

FIG. 5 explains the cannulation method of the present embodiment. In FIG. 5, a step of inserting the endoscope into the duodenum is performed, followed by a step of positioning the endoscope whereby the distal end section thereof is brought to the position where the papillary portion is in the field of view of the endoscope. For example, a step is performed where an operator recognizes the papillary portion from an endoscope image and positions the endoscope to the position where the papillary portion can be seen. Then, a step is performed where the drainage stimulant is administered to promote the secretion of pancreatic juice or bile. For example, a step is performed where an agent that promotes the secretion of pancreatic juice, such as secretin, is sprayed to the papillary portion from the distal end section of the endoscope. The drainage stimulant may be any agent that promotes the secretion of at least one of pancreatic juice and bile, and may be an agent that promotes the secretion of both pancreatic juice and bile. Then, a step is performed where a state of relaxation of the lumen in the papillary portion is confirmed, alternatively referred to as determining an amount of relaxation of the lumen in the papillary portion. The state of relaxation of the lumen in the papillary portion is, for example, a state of relaxation of the sphincter near the opening of the papillary portion, more specifically a state of relaxation of the sphincter of Oddi present around the papillary portion. In other words, a step is performed where it is confirmed whether the sphincter of Oddi in the papillary portion has been relaxed to allow for insertion of the cannula into the opening of the papillary portion. For example, FIG. 6 schematically shows a relaxed state and an unrelaxed state of the papillary portion. In an unrelaxed state, the opening is closed and insertion of the cannula is not easy, but in a relaxed state, the sphincter of Oddi is relaxed and open, facilitating insertion of the cannula into the opening (that is, an amount of relaxation can correspond e.g., to a size of the opening and/or an amount of pancreatic juice or bile present in the image(s)). For example, an operator or the like visually or otherwise confirms whether such a relaxed state is present, corresponding to an amount of relaxation. Subsequently, if the relaxed state (amount of relaxation) is greater than some predetermined amount of relaxation (e.g., open more than a predetermined amount) a step of cannulating the biliary duct is performed. That is, a step is performed where the cannula is protruded from the channel opening of the distal end section of the endoscope and the distal end of the cannula is inserted into the relaxed opening to thereby insert the cannula in the direction of the biliary duct. Then, a contrast radiography and imaging step is performed where a contrast agent is injected into the cannula and poured into the biliary duct from the distal end of the cannula.

Figure 7:
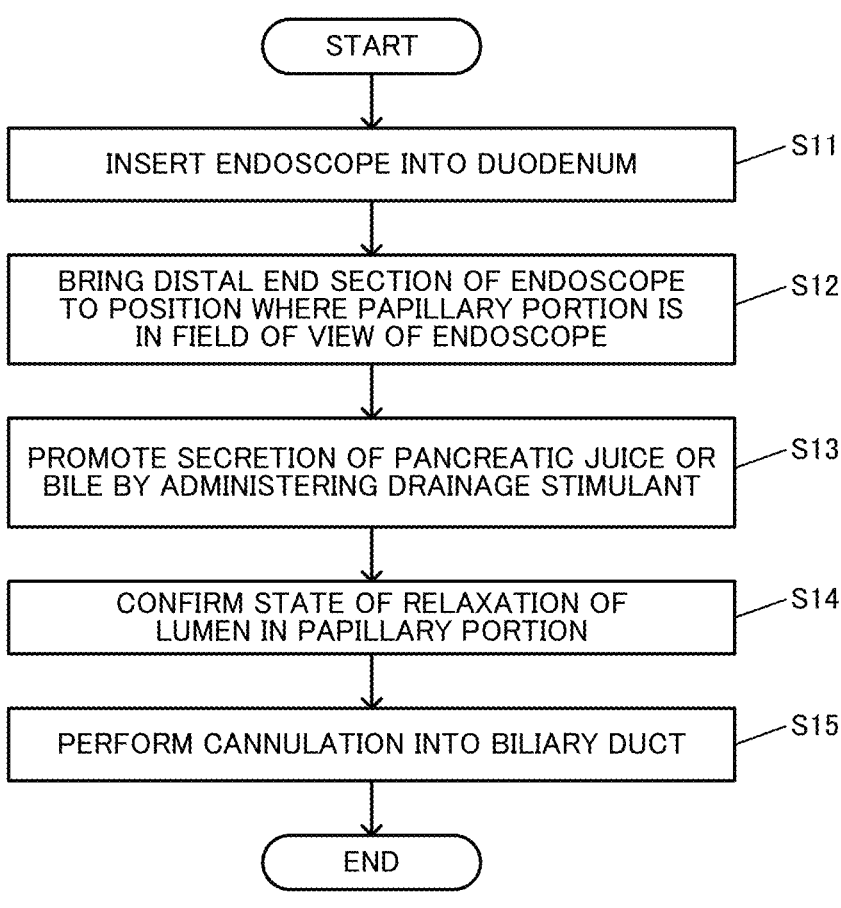
FIG. 7 is a flowchart explaining the cannulation method of the present embodiment.

FIG. 7 is a flowchart explaining the cannulation method of the present embodiment. As shown in FIG. 7, the cannulation method of the present embodiment includes step S11 of inserting the endoscope into the duodenum and step S12 of bringing the distal end section of the endoscope to the position where the papillary portion is in the field of view of the endoscope. These steps S11, S12 may be performed manually by an operator without electrical driving, or may be performed by electrically-driven endoscopic operation, which is detailed below. The cannulation method of the present embodiment further includes step S13 of promoting the secretion of pancreatic juice or bile by administering the drainage stimulant. Specifically, the drainage stimulant is administered to bring about the secretion of pancreatic juice or bile to thereby, for example, relax the sphincter of Oddi in the papillary portion. The cannulation method further includes step S14 of confirming a state of relaxation of the lumen in the papillary portion. For example, as shown in FIG. 6, it is confirmed whether the papillary portion is in an unrelaxed state or a relaxed state by determining whether the opening is greater than a predetermined size. This confirmation in step S14 may be performed by an operator visually checking the endoscope image, or may be implemented by a process of estimating a state of relaxation based on an endoscope image using an information processing system 20 of FIG. 11 described below. The cannulation method further includes step S15 of performing cannulation into the biliary duct. This cannulation step S15 may be performed manually by an operator without electrical driving power, or may be performed by electrically-driven endoscopic operation described below.

As described above, in the present embodiment, the cannulation method for ERCP includes the step of administering the drainage stimulant to promote the secretion of pancreatic juice or bile. Employing such a step can promote the secretion of pancreatic juice or bile by the drainage stimulant and relax the sphincter or the like in the papillary portion. This allows for easy insertion of the cannula into the opening of the papillary portion in the step of cannulating the biliary duct, facilitating an easier ERCP procedure.

Figure 8:
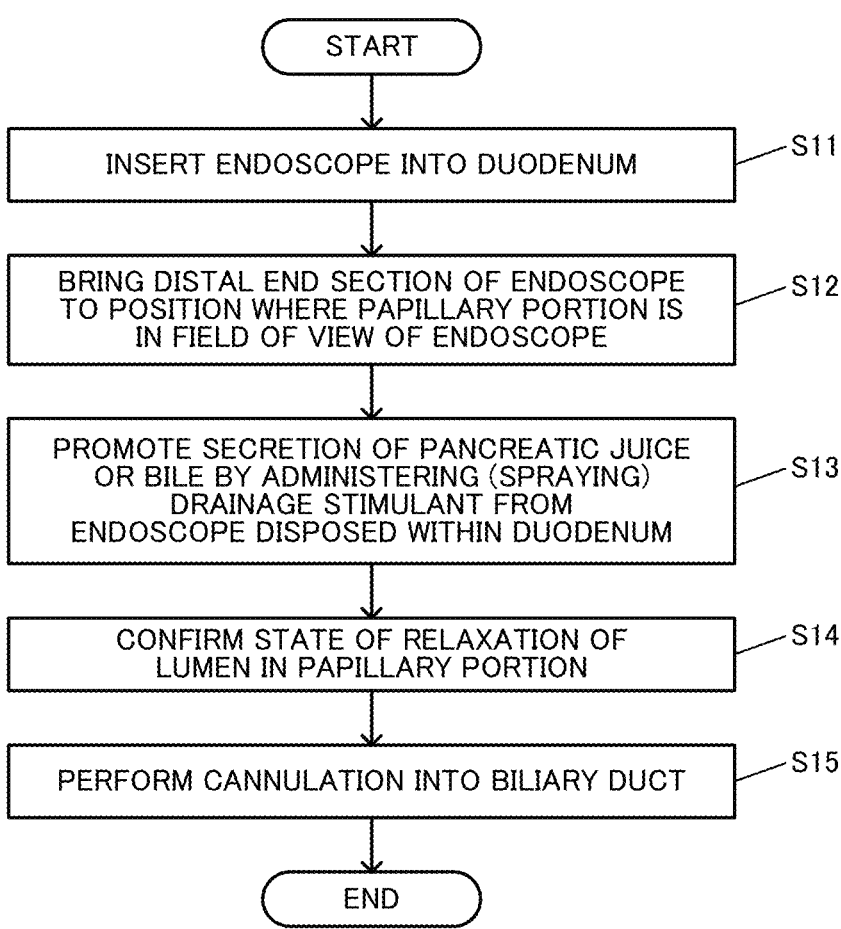
FIG. 8 is a flowchart explaining a specific example of the cannulation method of the present embodiment.

FIG. 8 is a flowchart explaining a specific example of the cannulation method of the present embodiment. FIG. 8 shows a specific example of step S13 in FIG. 7; in step S13 of promoting the secretion of pancreatic juice or bile, the drainage stimulant is administered (sprayed) from the endoscope disposed within the duodenum. For example, as shown in FIG. 5, an agent administration tube is protruded from the channel opening of the distal end section of the endoscope, and the drainage stimulant is administered from the tube. Specifically, an agent such as secretin is sprayed from the agent administration tube. The cannula may be substituted for this agent administration tube. In this way, the drainage stimulant can be administered to the papillary portion from the endoscope located close to the papillary portion in the duodenum, which allows for more precise administration of the drainage stimulant toward the papillary portion. Thus, this can relax the papillary portion in a more reliable manner, facilitating insertion of the cannula into the opening of the papillary portion.

In FIG. 8, following step S12 of bringing the distal end section of the endoscope to the above position, the drainage stimulant is administered from the endoscope to the papillary portion in step S13 of promoting the secretion of pancreatic juice or bile. For example, while the sequence of the steps in the cannulation method of the present embodiment, such as step 13 of promoting the secretion, may be in any order, in FIG. 8, the drainage stimulant is administered from the endoscope to the papillary portion in step S13 following step S12 of bringing the distal end section of the endoscope to the above position. This step sequence allows the drainage stimulant to be administered to the papillary portion from the endoscope whose distal end section has been brought to the position where the papillary portion is in the field of view of the endoscope. This allows for even more precise administration of the drainage stimulant toward the papillary portion, making it possible to relax the lumen in the papillary portion in an even more reliable manner.

Figure 9:
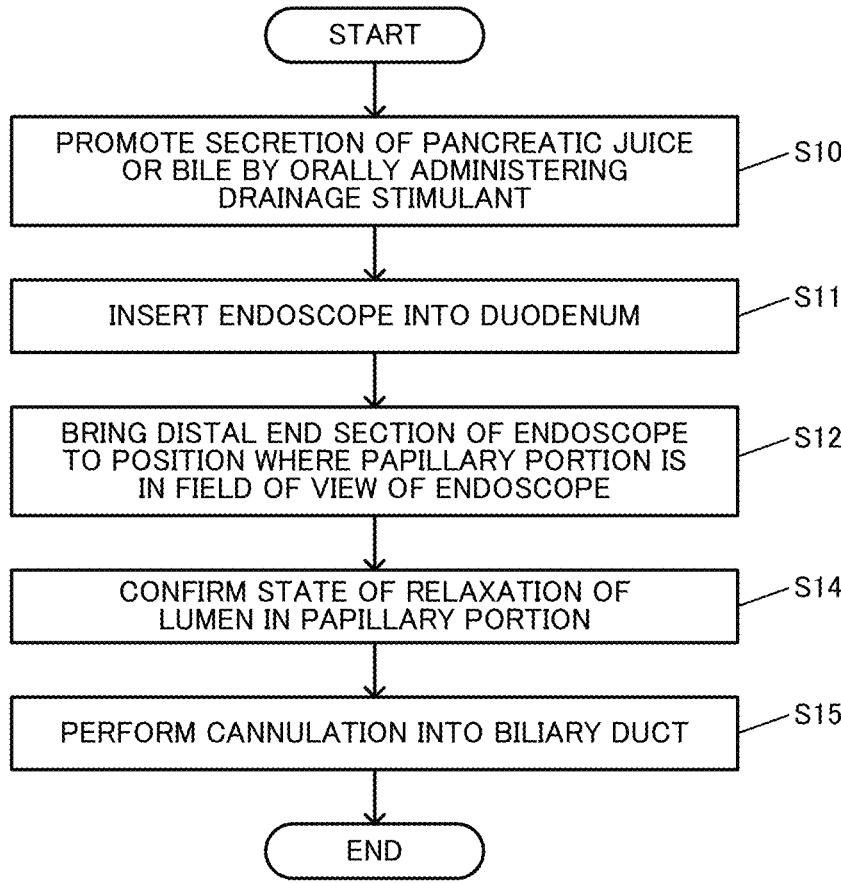
FIG. 9 is a flowchart explaining a specific example of the cannulation method of the present embodiment.

FIG. 9 is a flowchart explaining another specific example of the cannulation method of the present embodiment. In FIGS. 7 and 8, step S13 of promoting the secretion of pancreatic juice or bile is employed following step S12 of bringing the distal end section of the endoscope to the above position. In FIG. 9, in contrast, step S10 of promoting the secretion of pancreatic juice or bile is employed prior to step S11 of inserting the endoscope into the duodenum. For example, in FIG. 9, step S10 of promoting the secretion of pancreatic juice or bile employs a step of orally administering the drainage stimulant prior to step S11 of inserting the endoscope. For example, after a patient has taken the drainage stimulant that stimulates the secretion of pancreatic juice or bile, step S11 is performed to insert the endoscope into the duodenum, and then step S12 is performed to bring the distal end section of the endoscope to the position where the papillary portion is in the field of view of the endoscope. Then, step S14 is performed to confirm a state of relaxation of the lumen in the papillary portion, and step S15 is performed to cannulate the biliary duct. This step sequence can promote the secretion of pancreatic juice or bile through oral administration of the drainage stimulant prior to the insertion of the endoscope, without needing to provide a mechanism to spray the agent directly to the papillary portion from the distal end section of the endoscope. Thus, the oral administration of the drainage stimulant can relax the lumen in the papillary portion, facilitating insertion of the cannula into the opening of the papillary portion.

Figure 10:
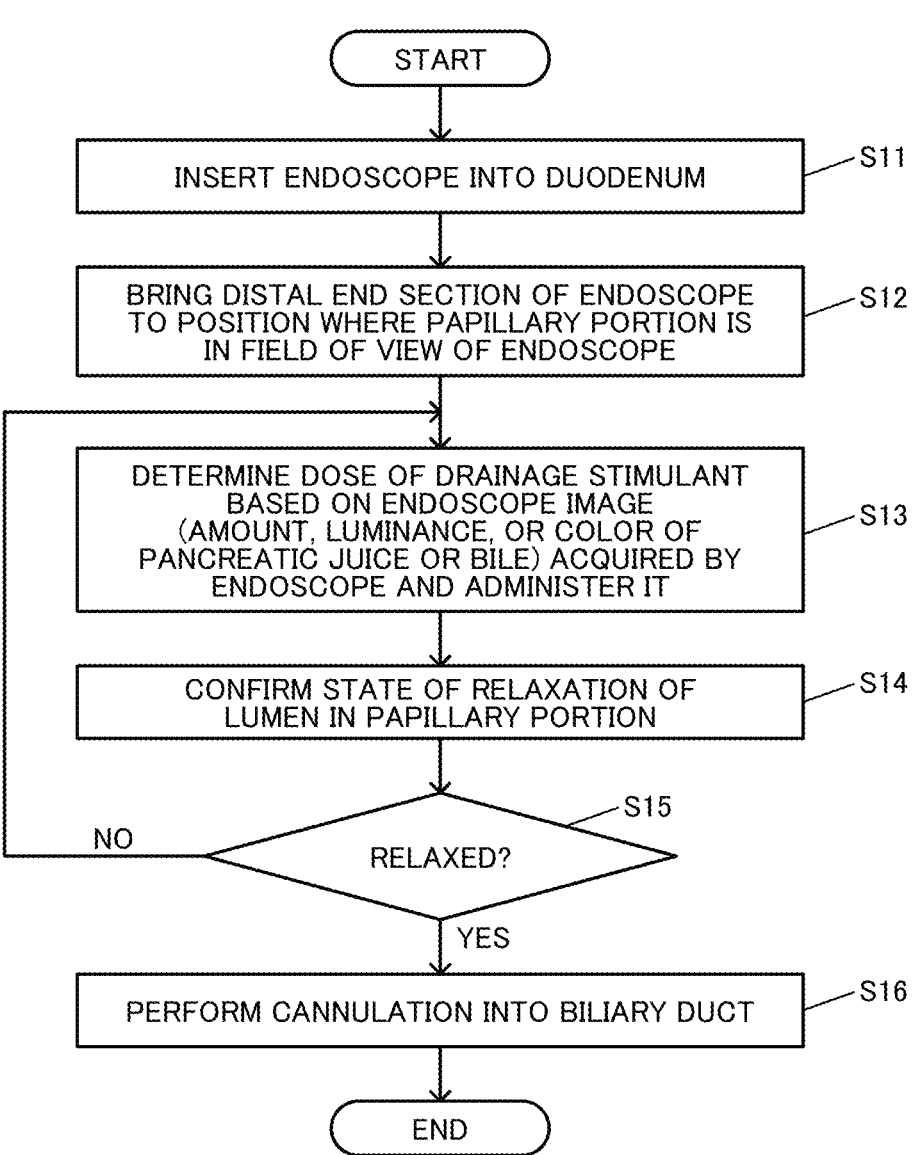
FIG. 10 is a flowchart explaining a specific example of the cannulation method of the present embodiment.

FIG. 10 is a flowchart explaining another specific example of the cannulation method of the present embodiment. In FIG. 10, a dose of the drainage stimulant is determined based on an endoscope image acquired by the endoscope and administered accordingly in step S13. For example, a dose of the drainage stimulant is determined based on an amount, luminance, or color of pancreatic juice or bile shown in the endoscope image and administered accordingly. Then, in step S14, a state (or amount) of relaxation of the lumen in the papillary portion is confirmed, and upon determining in step S15 that the lumen is relaxed, cannulation into the biliary duct is performed in step S16. On the other hand, upon determining in step S15 that the lumen is not relaxed, the process returns to step S13 to administer the drainage stimulant again.

As described above, in FIG. 10, the dose of the drainage stimulant is determined based on the endoscope image acquired by the endoscope in step 13 of promoting the secretion of pancreatic juice or bile. For example, the dose of the drainage stimulant is determined through a process of determining a state of relaxation based on the endoscope image as described below. Specifically, the endoscope image is input to a trained model to determine a state of relaxation of the lumen in the papillary portion. Alternatively, an operator visually inspects the endoscope image to determine the dose of the drainage stimulant. Upon determining that the lumen in the papillary portion has been relaxed by administration of the determined dose of the drainage stimulant, cannulation into the biliary duct is performed. In this way, the endoscope image acquired by the endoscope can be effectively utilized to relax the lumen in the papillary portion by administration of the appropriate dose of the drainage stimulant determined based on the endoscope image. Thus, the operator can easily insert the cannula into the opening of the papillary portion which has been relaxed by administration of the appropriate dose of the drainage stimulant.

In this case, in step S13 of promoting the secretion of pancreatic juice or bile, the cannulation method of the present embodiment can determine the dose of the drainage stimulant based on at least one of the amount, luminance, or color of pancreatic juice or bile shown in the endoscope image. This allows for using the amount, luminance, or color of pancreatic juice or bile in the endoscope image to determine the dose of the drainage stimulant by which the lumen in the papillary portion can be relaxed. Thus, the lumen in the papillary portion can be relaxed by administration of the appropriate dose of the drainage stimulant, facilitating insertion of the cannula into the opening of the papillary portion. For example, when the amount of pancreatic juice or bile shown in the endoscope image is small, the dose of the drainage stimulant is increased. On the other hand, when the amount of pancreatic juice or bile shown in the endoscope image is large, the dose of the drainage stimulant is reduced. This is because the larger the amount of pancreatic juice or bile, the more relaxed state the papillary portion is considered to be in. Also, when a large amount of pancreatic juice or bile is secreted, light from the light source or the like at the distal end section of the endoscope is reflected by the liquid, so that the luminance of the liquid portion in the endoscope image changes. Thus, the dose of the drainage stimulant can be determined based on the luminance of pancreatic juice or bile. The dose of the drainage stimulant can also be determined by detecting the color of pancreatic juice or bile and determining the amount (drainage amount) of pancreatic juice or bile. For example, the color of bile is yellow, yellow-green, brown, or amber. As such, detection of these colors in the endoscope image allows for determining the amount of pancreatic juice or bile to determine the dose of the drainage stimulant. Also, when pancreatic juice or bile is secreted in the lumen in the papillary portion, the color of the biological tissue in the lumen and the color of pancreatic juice or bile are mixed and displayed in the endoscope image, so that detection of such changes in the color allows for determining the amount of pancreatic juice or bile to determine the dose of the drainage stimulant.

The drainage stimulant is, for example, an agent that promotes the secretion of pancreatic juice, which is e.g., secretin. Secretin is a gastrointestinal hormone that is synthesized in the mucous membrane of small intestine and promotes exocrine secretion of bicarbonate from the pancreas. For example, secretin is an agent that promotes the drainage of pancreatic juice. While the cannula is inserted into the biliary duct, the biliary and pancreatic ducts are connected and merged at the confluence. Accordingly, using an agent that promotes the drainage of pancreatic juice is expected to be effective in relaxing the papillary portion.

The drainage stimulant may be an agent that promotes the secretion of bile. For example, curcumin is an agent that promotes the drainage of bile. Curcumin is a yellow polyphenol compound contained in turmeric and the like. Also, cholecystokinin (CCK) is an agent that promotes the drainage of both pancreatic juice and bile and thus can be used as an agent to promote bile secretion. CCK is a gastrointestinal hormone that is secreted from the upper small intestine and controls secretion of gastric acid, pancreatic juice, and bile after meals.

For example, the sphincter of Oddi in the papillary portion becomes relaxed upon stimulating the drainage of bile and pancreatic juice. Bile and pancreatic juice are drained as the gastrointestinal hormones produced in the duodenum, which are CCK and secretin, respectively, enter the bloodstream and act on the brain. CCK is more effective because it stimulates the drainage of both bile and pancreatic juice. For example, gastrointestinal hormones are peptides, which are difficult to produce in a stable manner. Additionally, intra-venous injections are required because they are degraded by digestive fluids when administered orally. On the other hand, secretin is widely used as a pancreatic drainage stimulant and suitable as an agent for relaxing the sphincter of Oddi and facilitating the ERCP.

For example, when food is digested in the stomach and reaches the duodenum as acids, secretin is secreted by intestinal cells and carried in the bloodstream to the brain, stimulating the secretion of pancreatic juice from the pan-creas. Accordingly, administering secretin to the papillary portion can promote the secretion of pancreatic juice. On the other hand, when lipids reach the duodenal lumen, cholecys-tokinin-pancreozymin (CCK-PZ) is produced and internally secreted from the duodenum. Then, an elevated blood con-centration of CCK-PZ causes the gallbladder to contract, causing more bile to flow into the duodenum. Pancreatic juice rich in digestive enzymes is also produced and exter-nally secreted. These factors act to digest and degrade lipids in the duodenal lumen, bringing it back into the state it was in before the arrival of lipids. Thus, CCK is considered to be capable of promoting the secretion of both pancreatic juice and bile.

As described above, secretin is secreted as acids reach the duodenum, and CCK is secreted as lipids reach the duode-num. Accordingly, lipids and acids, either in the form of a liquid mixture thereof or individually, are endoscopically sprayed to the duodenum, and the drainage of bile is visually or otherwise confirmed. Then, cannulation is performed. As such, cannulation can be performed with the sphincter of Oddi relaxed. Additionally, lipids that easily cause secretion of CCK are known, and spraying such lipids from the distal end section of the endoscope or orally administering them prior to the ERCP is expected to promote the secretion of pancreatic juice and bile.

It is also possible to administer substances that cause bile itself to drain. Examples of substances effective in stimu-lating the drainage of bile include curcumin (turmeric or *Curcuma longa*). Curcumin is administered orally prior to implementing the ERCP and the endoscope is inserted. Then, upon confirming that bile is drained from the papillary portion, cannulation is performed.

Information Processing System

As described with reference to FIGS. 3 and 4, the shapes of the opening and its surroundings in the papillary portion differ from individual to individual. Accordingly, it is dif-ficult for operators to determine a state of relaxation of the papillary portion through visual confirmation. For example, inexperienced operators may be unable to properly deter-mine whether the papillary portion has become relaxed.

Hence, the present embodiment employs a procedure of estimating a state of relaxation of the lumen in the papillary portion based on an endoscope image to determine whether or not or how much to administer the drainage stimulant.

Figure 11:
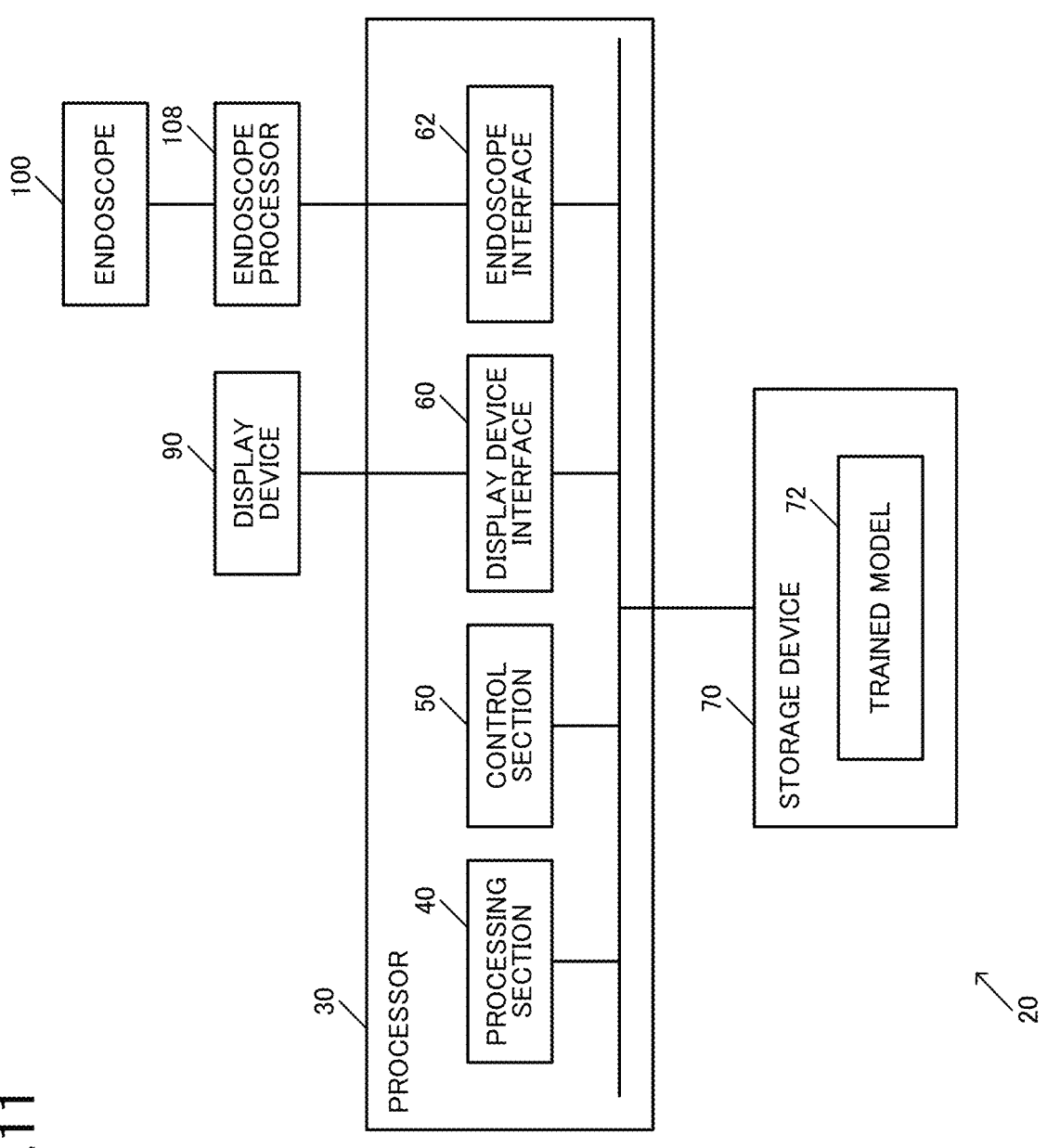
FIG. 11 shows a configuration example of an information processing system of the present embodiment.

FIG. 11 shows a configuration example of an information processing system 20 for implementing such a procedure of the present embodiment.

As shown in FIG. 11, the information processing system 20 includes a processor 30. The information processing system 20 can further include a storage device 70. For example, this information processing system 20 can be implemented by a control device 600 of a medical system 10 described below with reference to FIG. 21. In this case, the medical system 10 is implemented by an endoscope 100 and the information processing system 20. In this case, part or all of the information processing system 20 may be, for example, implemented by a drive control device 200 and a video control device 500 of the control device 600, or by an information processing device, such as a personal computer (PC), provided to the control device 600 separately from the drive control device 200 and the video control device 500. Alternatively, part or all of the information processing system 20 may be implemented by a server or the like in a cloud system.

The processor 30 includes hardware. The hardware of the processor 30 may be implemented by digital circuitry that processes digital signals, or by digital circuitry and analog circuitry that processes analog signals. The processor 30 can also be implemented by one or more circuit devices (ICs) or one or more circuit elements mounted on a circuit board. Specifically, the processor 30 can be implemented by a central processing unit (CPU), for example. However, the processor 30 is not limited to a CPU and may be imple-mented by any of various processors including a graphics processing unit (GPU) and a digital signal processor (DSP). Alternatively, the processor 30 may be implemented by hardware circuitry including an ASIC.

The storage device 70 is a device that stores information, which is e.g., a memory. The storage device 70 as a storage section can be implemented by a semiconductor memory such as SRAM and DRAM. Alternatively, the storage device 70 may be implemented by a magnetic storage device, such as a hard disk drive (HDD), or by an optical storage device. For example, the storage device 70 serves as a working area for processes executed by the processor 30. For example, the storage device 70 stores computer-readable instructions, and execution of the instructions by the processor 30 implements processing in the respective sections of the information processing system 20. The instructions as referred to herein may be a set of instructions constituting a program, or may be instructions that direct the hardware circuitry of the processor 30 to operate.

The processor 30 includes a processing section 40. The processor 30 can also include a control section 50, a display device interface 60, and an endoscope interface 62. The processing section 40 performs processes including estimat-ing a state of relaxation of the papillary portion and deter-mining whether or not or how much the drainage stimulant should be administered, e.g., by determining a size of the opening in the image(s) and comparing the same to a predetermined size opening stored in the storage. The con-trol section 50 controls electrically-driven endoscopic operation. Details of the processing section 40 and the control section 50 are described below.

The display device interface 60 is an output section to output display images and interfaces with the display device 90. For example, data of display images generated by the processor 30 are output to the display device 90 via the display device interface 60 and displayed on the display device 90. The endoscope interface 62 is an image acqui-sition section and interfaces with endoscope 100. Specifically, the endoscope interface 62 interfaces with an endoscope processor 108 that performs various processing associated with the endoscope 100. For example, the processor 30 acquires endoscope images captured by the endoscope 100 via the endoscope interface 62. In this case, the endoscope processor 108 performs various processing on the endoscope images, such as image processing. The endoscope processor 108 is implemented by the video control device 500 in FIG. 21 (described below) or the like. The display device 90 can be implemented by, for example, a liquid crystal display (LDC), an organic EL display, or a CRT display. Details of the endoscope 100 are described below.

Figure 12:
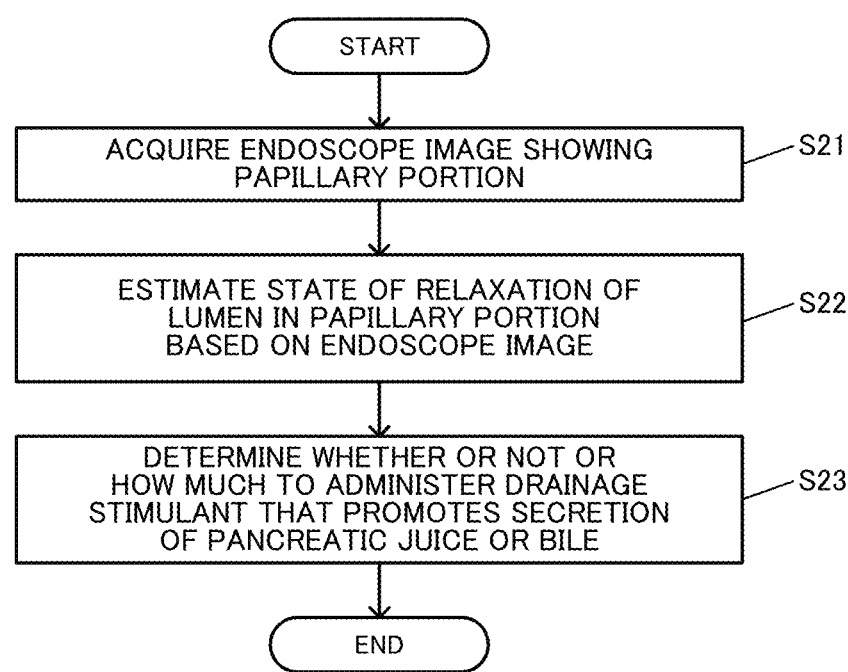
FIG. 12 is a flowchart explaining a process of the present embodiment.

FIG. 12 is a flowchart explaining a process of the present embodiment. As shown in FIG. 12, the processor 30 including the hardware (the processing section 40; the same applies below) acquires an endoscope image showing the papillary portion 100 from the endoscope 100 (step S21). For example, the processor 30 acquires the endoscope image (endoscope video) captured by the endoscope 100 through the endoscope interface 62. The processor 30 then estimates a state of relaxation of the lumen in the papillary portion based on the endoscope image acquired (step S22). For example, the processor 30 estimates a state of relaxation of the sphincter near the opening of the papillary portion based on the endoscope image showing the papillary portion, e.g., based on a determined size of the opening in the image(s) and/or an amount of pancreatic juice or bile present in the image(s). The processor 30 then determines whether or not or how much to administer the drainage stimulant that promotes the secretion of pancreatic juice or bile (step S23). For example, the processor 30 determines whether a state of relaxation of the papillary portion requires administration of the drainage stimulant or what dose of the drainage stimulant should be administered to bring about a relaxed state suitable for cannulation. For example, the processor 30 determines whether the papillary portion has been in a relaxed state suitable for cannulation without any administration of the drainage stimulant, or whether the papillary portion will not be in a relaxed state suitable for cannulation without administration of the drainage stimulant. Alternatively, the processor 30 determines whether the papillary portion has been in a relaxed state suitable for cannulation after administration of the drainage stimulant and no additional administration of the drainage stimulant is needed, or whether the papillary portion will not be in a relaxed state suitable for cannulation without additional administration of the drainage stimulant. The processor 30 also determines what dose of the drainage stimulant should be administered to bring about a relaxed state suitable for cannulation, based on conditions of the papillary portion and its surroundings shown in the endoscope image. It should be noted that the processor 30 is required to determine at least one of whether or not to administer the drainage stimulant and how much to administer the drainage stimulant, and may determine both whether or not and how much to administer the drainage stimulant. The processing section 40 performs the process of estimating a state of relaxation of the papillary portion and determining whether or not or how much to administer the drainage stimulant.

As described above, in the present embodiment, a state of relaxation of the lumen in the papillary portion is estimated from the endoscope image showing the papillary portion, and whether or not or how much to administer the drainage stimulant is determined. In this way, upon determination that administration of the drainage stimulant is needed, the drainage stimulant is administered to promote the secretion of pancreatic juice or bile, making it possible to relax the sphincter and the like in the papillary portion. Additionally, the determined dose of the drainage stimulant is administered to promote the secretion of pancreatic juice or bile, making it possible to sufficiently relax the sphincter and the like in the papillary portion. This allows for easy insertion of the cannula into the opening of the papillary portion in cannulating the biliary duct, facilitating an easier ERCP procedure.

As shown in FIG. 5, the storage device 70 stores a trained model 72. Specifically, the storage device 70 stores a trained model 72 trained to output information about whether or not to administer the drainage stimulant or information about how much to administer the drainage stimulant in response to an endoscope image. The information about whether or not to administer the drainage stimulant is information indicating whether the administration of the drainage stimulant is needed, and may be information about the need for administration itself or information for identifying whether the administration is needed. The information about how much to administer the drainage stimulant is information indicating the dose of the drainage stimulant, and may be information about the dose itself, or may be information for identifying the dose. The processor 30 (the processing section 40) determines whether or not or how much to administer the drainage stimulant based on the endoscope image and the trained model 72. For example, the processor 30 inputs an endoscope image to the trained model 72 and determines whether or not or how much to administer the drainage stimulant based on information output from the trained model 72 about whether or not to administer the drainage stimulant or how much to administer the drainage stimulant.

Thus, the trained model 72 can be used estimate a state of relaxation of the lumen in the papillary portion and determine whether or not or how much to administer the drainage stimulant based on the endoscope image. This facilitates insertion of the cannula into the opening of the papillary portion in cannulating the biliary duct.

Here, the trained model 72 is a machine learned model built using training data and is implemented with, for example, a neural network. For example, the trained model 72 is trained with training data that is a data set in which input data are associated with ground truth data. For example, the storage device 70 stores a program describing an inference algorithm and parameters used in the inference algorithm as information of the trained model 72. The processor 30 then performs processing based on the information of the trained model 72. That is, the processor 30 executes the program using the parameters stored in the storage device 70 to perform the process of determining whether or not or how much to administer the drainage stimulant based on an endoscope image. For example, the inference algorithm can employ a neural network. Weight coefficients for inter-connected nodes in the neural network are the parameters. The neural network includes an input layer to which input data is fed, an intermediate layer that performs arithmetic processing on the data fed through the input layer, and an output layer that outputs recognition results based on the arithmetic processing results output from the intermediate layer. The inference algorithm is not limited to the neural network, and can employ various machine learning processing used for the recognition process. The trained model 72 is generated by a learning device. The learning device generates the trained model 72 by inputting training data, also called teacher data, into a learning model and providing feedback to the learning model based on its inference results. The training data includes a plurality of data sets, and each set includes input data and ground truth data. The ground truth data refers to the inference results that should be obtained for the input data, and is prepared in advance by, for example, medical professionals.

For example, the input data for the trained model 72 in the present embodiment is endoscope images from the endoscope 100. The ground truth data for the trained model 72 is data for estimating and determining whether or not or how much to administer the drainage stimulant. For example, the ground truth data is data that indicates whether the administration of the drainage stimulant is needed or data that identifies the dose of the drainage stimulant.

Figure 13:
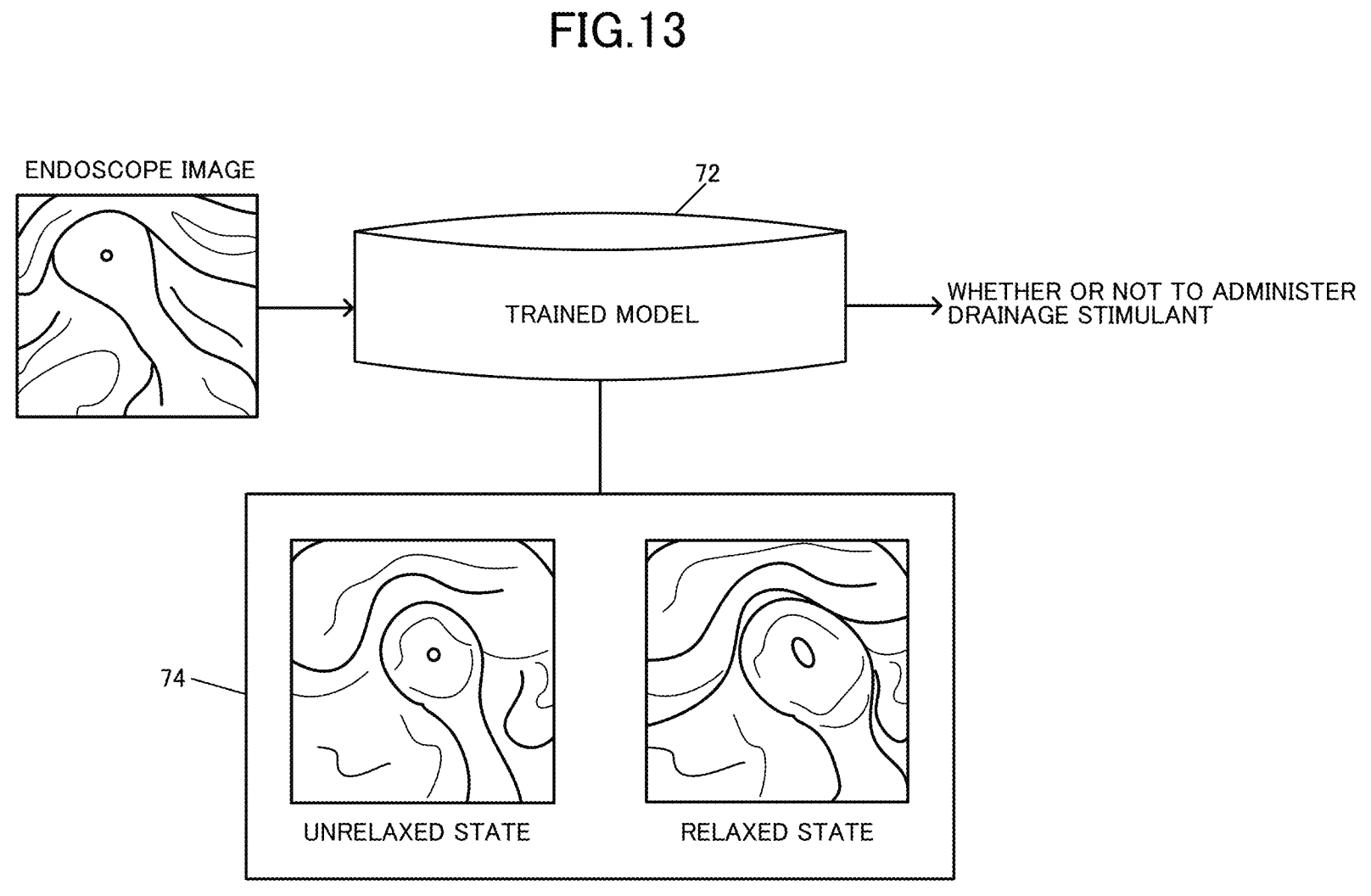

FIG. 13 illustrates an example process of the present embodiment using the trained model 72. In FIG. 13, the trained model 72 is trained with training data 74, in which endoscope images are associated with information indicating whether or not to administer the drainage stimulant. For example, the training data 74 is created by a medical professional, such as a physician, judging a state of relaxation of the papillary portion in each of multiple training endoscope images and assigning to each endoscope image the information indicating whether or not to administer the drainage stimulant as a ground truth label. For example, the medical professional observes the image of the papillary portion in each endoscope image, judges whether it is relaxed enough to enable easy insertion of the cannula, and assigns the information indicating whether or not to administer the drainage stimulant as the ground truth label. Thus, during inference, in response to input of, for example, an endoscope image showing the papillary portion in an unrelaxed state or an endoscope image showing the papillary portion in an insufficiently relaxed state that will make it impossible to easily insert the cannula, the trained model 72 outputs information indicating that the administration of the drainage stimulant is needed. Also, during inference, in response to input of, for example, an endoscope image showing the papillary portion relaxed enough to enable easy insertion of the cannula, the trained model 72 outputs information indicating that the administration of the drainage stimulant is not needed.

As described above, in FIG. 13, the trained model 72 outputs the information indicating whether or not to administer the drainage stimulant for endoscope images showing the papillary portion, so that the processor 30 can determine whether or not to administer the drainage stimulant based on the information output from the trained model 72 and provide instructions to administer the drainage stimulant, not to administer it, or to complete the administration. For example, the processor 30 provides to an operator a notification instructing him/her to administer the drainage stimulant, not to administer it, or to complete the administration. Alternatively, in cases where the medical system 10 automatically administers the drainage stimulant, the processor 30 instructs a mechanism (spraying mechanism) that administers (sprays) the drainage stimulant to administer it, not to administer it, or to complete the administration.

Figure 14:
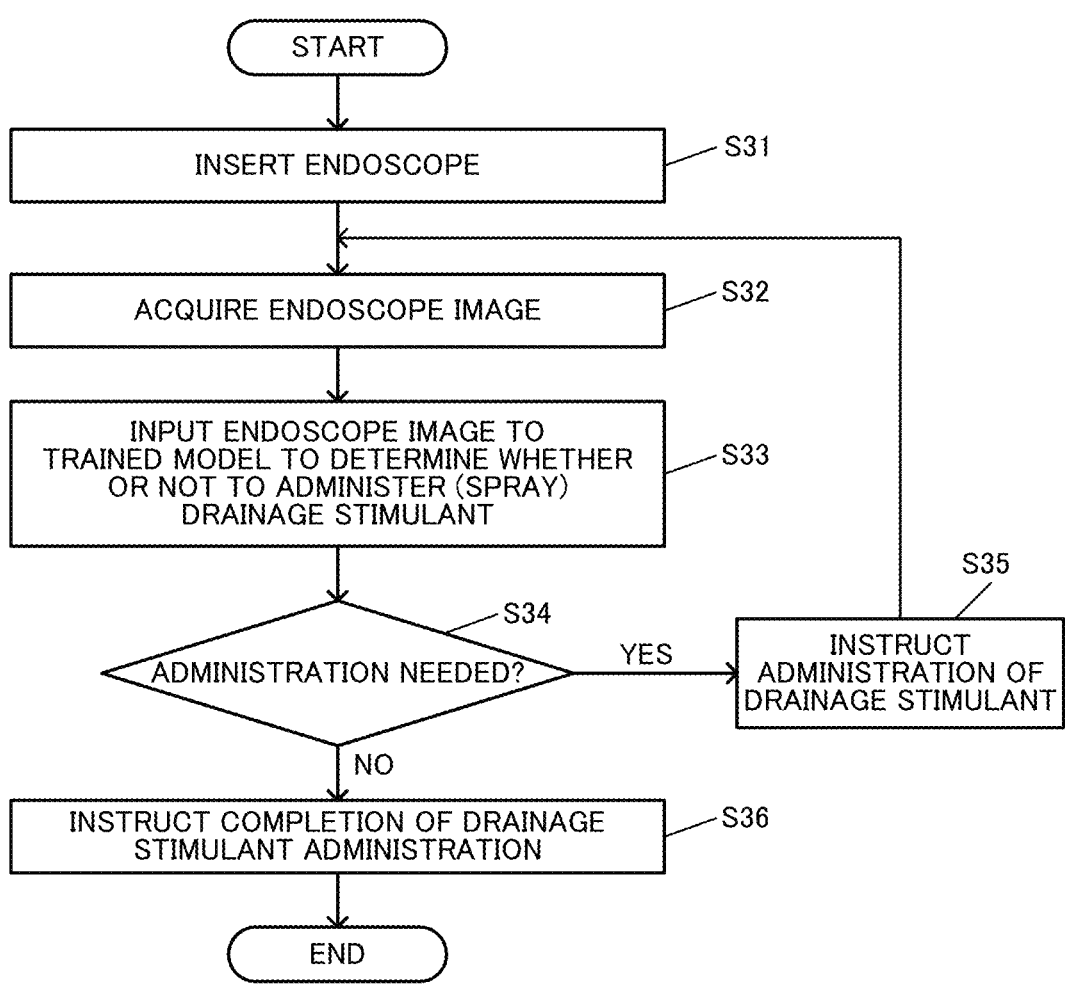
FIG. 14 is a flowchart explaining a process of the present embodiment when the trained model is used.

FIG. 14 is a flowchart illustrating a process of the present embodiment when the trained model 72 in FIG. 13 is used. First, the endoscope is inserted (step S31), and the processor 30 (the processing section 40) acquires an endoscope image (step S32). The processor 30 then inputs the endoscope image to the trained model 72 to determine whether or not to administer (spray) the drainage stimulant (step S33). For example, the processor 30 determines whether or not to administer the drainage stimulant by estimating a state of relaxation of the papillary portion using the trained model 72. If it is determined that the administration of the drainage stimulant is needed, the processor 30 instructs the administration of the drainage stimulant (step S35) and moves to, for example, step S32. For example, the processor 30 provides a notification to the operator instructing him/her to administer the drainage stimulant, or automatically administers the drainage stimulant. On the other hand, if it is determined that the administration of the drainage stimulant is not needed, the processor 30 instructs completion of the drainage stimulant administration (step S36). For example, the processor 30 provides a notification to the operator instructing him/her to complete the drainage stimulant administration, or automatically completes the drainage stimulant administration.

Figure 15:
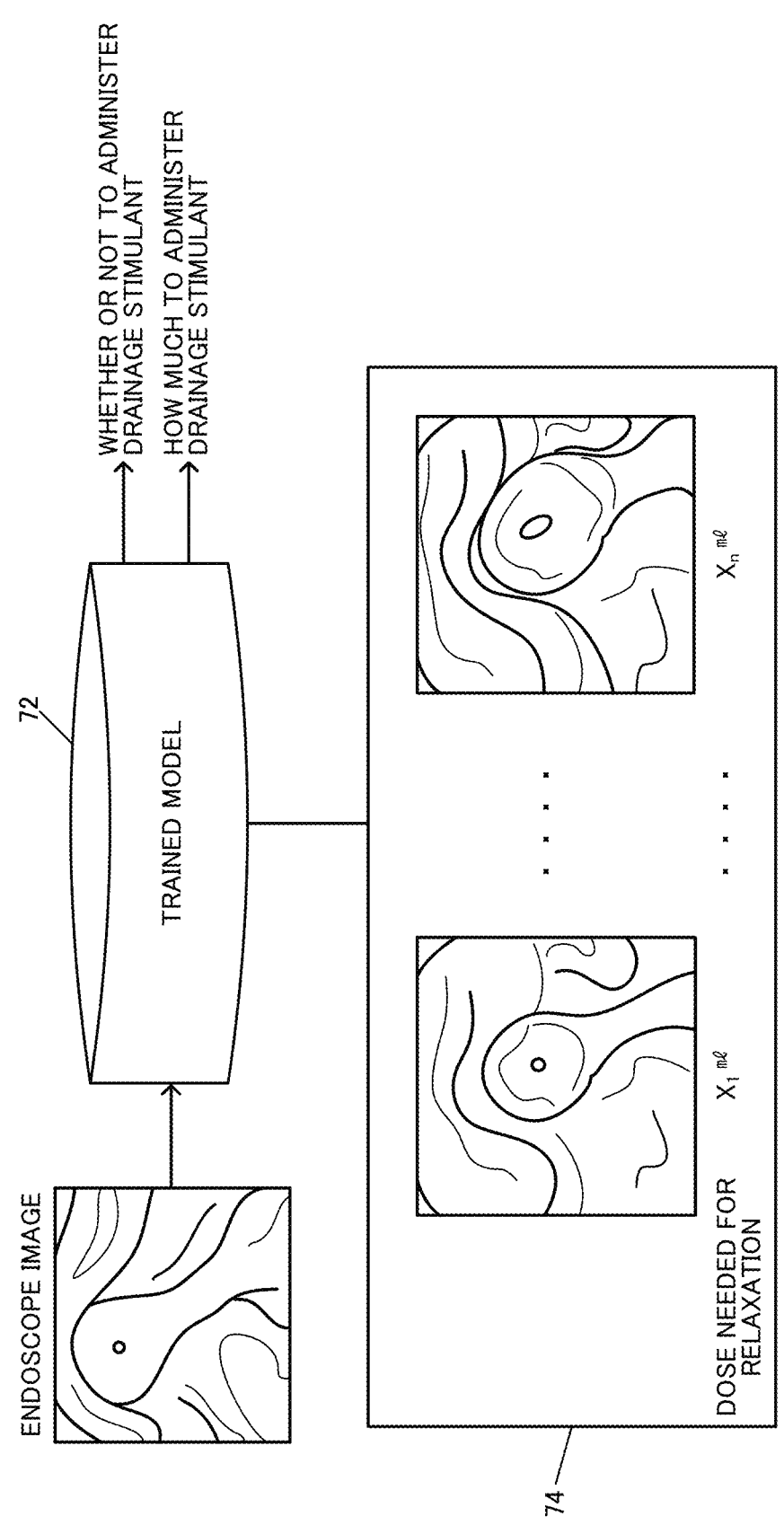
FIG. 15 explains another process using the trained model.

FIG. 15 explains another example process of the present embodiment using the trained model 72. In FIG. 15, the trained model 72 is trained with the training data 74, in which endoscope images are associated with drainage stimulant doses. For example, the training data 74 is created by a medical professional, such as a physician, judging a state of relaxation of the papillary portion in each of multiple training endoscope images and assigning to each endoscope image information indicating a dose of the drainage stimulant as a ground truth label. For example, the medical professional observes the image of the papillary portion in each endoscope image, determines what dose of the drainage stimulant should be administered to bring the papillary portion into a relaxed state suitable for cannulation, and assigns the information indicating the dose of the drainage stimulant as the ground truth label. Thus, in response to input of an endoscope image during inference, the trained model 72 outputs information about the dose of the drainage stimulant corresponding to that endoscope image. For example, the trained model 72 outputs information about the dose of the drainage stimulant by which the papillary portion can be brought into a suitable relaxed state.

As described above, in FIG. 15, the trained model 72 outputs the information indicating the dose of the drainage stimulant for the endoscope image showing the papillary portion, so that the processor 30 can determine the dose of the drainage stimulant based on the information output from the trained model 72 and indicate the dose of the drainage stimulant. For example, the processor 30 provides to an operator a notification indicating the dose of the drainage stimulant needed to relax the papillary portion. Alternatively, in cases where the medical system 10 automatically administers the drainage stimulant, the processor 30 indicates the dose of the drainage stimulant to a mechanism (spraying mechanism) that administers (sprays) the drainage stimulant. In FIG. 15, the trained model 72 also outputs information about whether or not to administer the drainage stimulant, and the processor 30 determines whether or not to administer the drainage stimulant based on this information.

Figure 16:
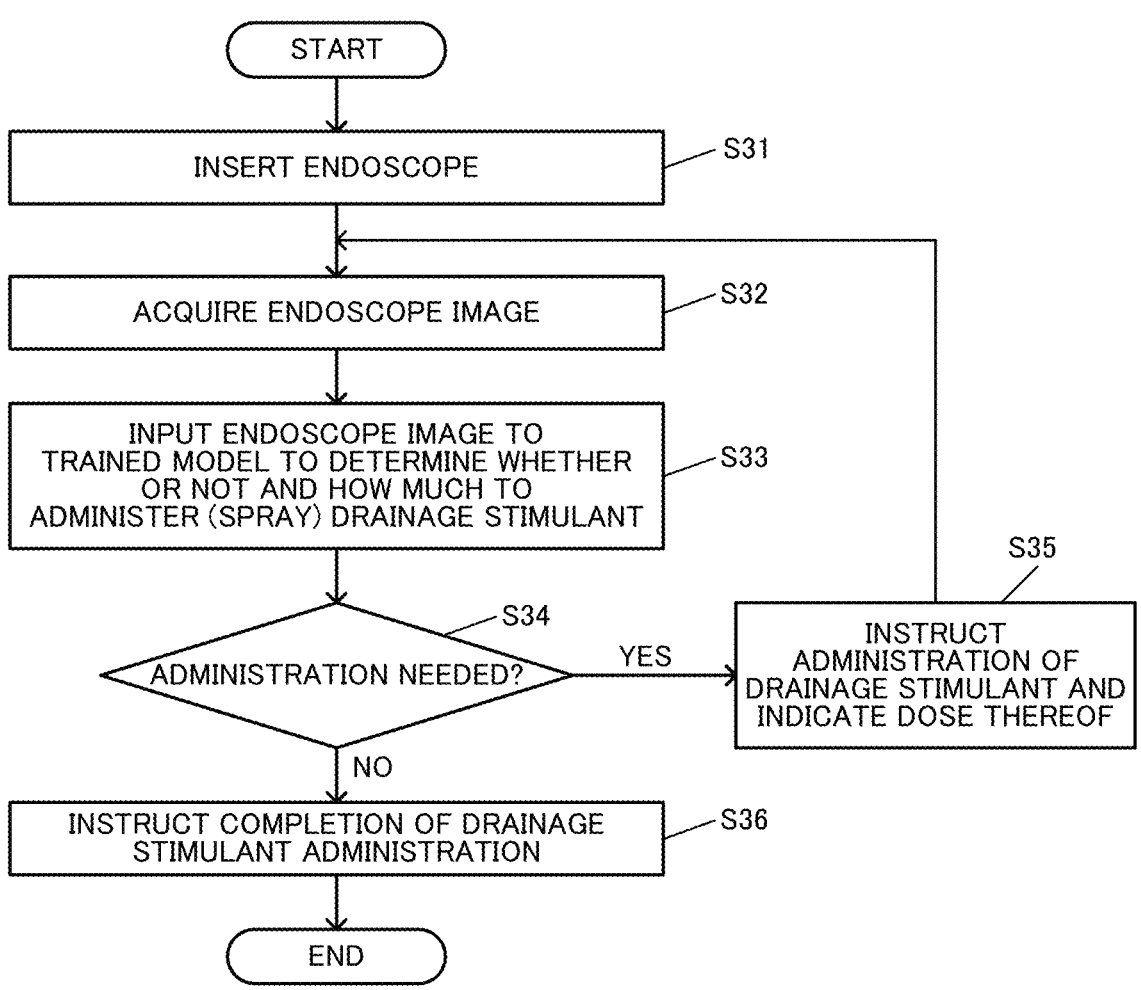
FIG. 16 is a flowchart explaining another process of the present embodiment when the trained model is used.

FIG. 16 is a flowchart of a process of the present embodiment when the trained model 72 in FIG. 15 is used. FIG. 16 differs from FIG. 14 in that, in step S33 of FIG. 16, the processor 30 inputs an endoscope image to the trained model 72 to determine whether or not to administer (spray) the drainage stimulant and how much to administer (spray) the drainage stimulant. If it is determined in step S34 that the administration is needed, the processor 30 instructs the administration of the drainage stimulant and indicates the dose thereof in step S35. If it is determined that the administration is not needed, the processor 30 instructs completion of the drainage stimulant administration in step S36.

Figure 17:
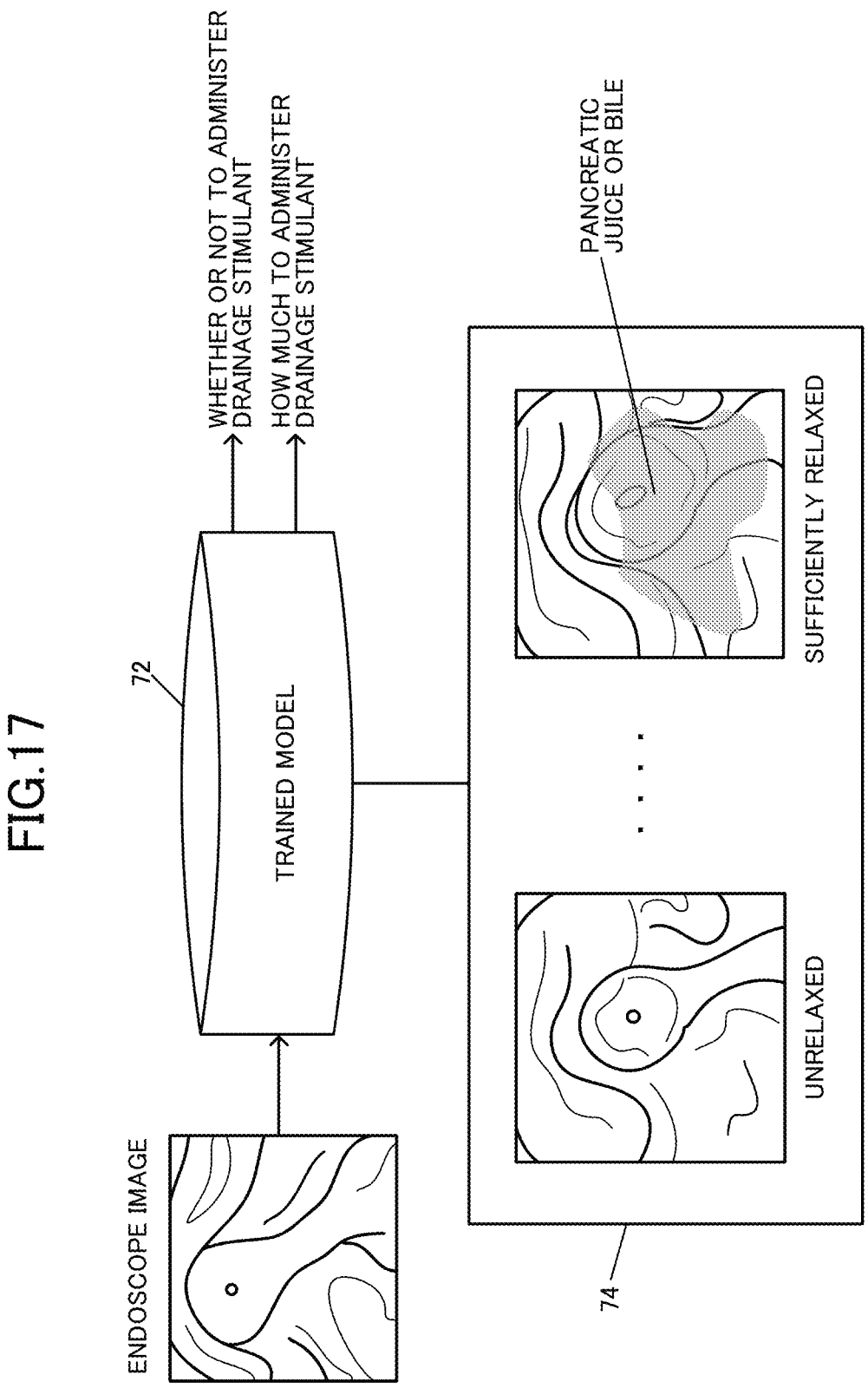
FIG. 17 explains another process using the trained model.

FIG. 17 illustrates another example process of the present embodiment using the trained model 72. The trained model 72 in FIG. 17 is trained also using information about the drainage amount of pancreatic juice or bile, for example, trained with the training data 74 based on information about the drainage amount of pancreatic juice or bile. For example, the trained model 72 is trained to estimate a state of relaxation of the papillary portion based on the drainage amount of pancreatic juice or bile shown in the endoscope image. For example, the drainage amount of pancreatic juice or bile can be evaluated by extracting from the endoscope image color regions corresponding to pancreatic juice or bile. For example, bile can be evaluated by extracting regions of transparent dark brown, green, or intermediate colors therebetween, or regions of white turbid liquids, and pancreatic juice can be evaluated based on changes in luminance because pancreatic juice is clear and colorless. For example, when it is determined from the endoscope image that a large amount of pancreatic juice or bile is drained, the papillary portion is estimated to be sufficiently relaxed. The trained model 72 outputs information about whether or not or how much to administer the drainage stimulant based on the estimated drainage amount of pancreatic juice or bile. For example, when a small amount of pancreatic juice or bile is drained, the trained model 72 outputs information instructing administration of the drainage stimulant. When a large amount of pancreatic juice or bile is drained, the trained model 72 outputs information instructing completion of the drainage stimulant administration. Alternatively, the trained model 72 may learn a relation between the drainage amount of pancreatic juice or bile and the dose of the drainage stimulant. For example, the trained model 72 learns the dose needed to sufficiently drain the pancreatic juice or bile to bring about a relaxed state suitable for cannulation. The trained model 72 then outputs information about the dose of the drainage stimulant needed to sufficiently drain the pancreatic juice or bile to transition the current state into a relaxed state suitable for cannulation.

Figure 18:
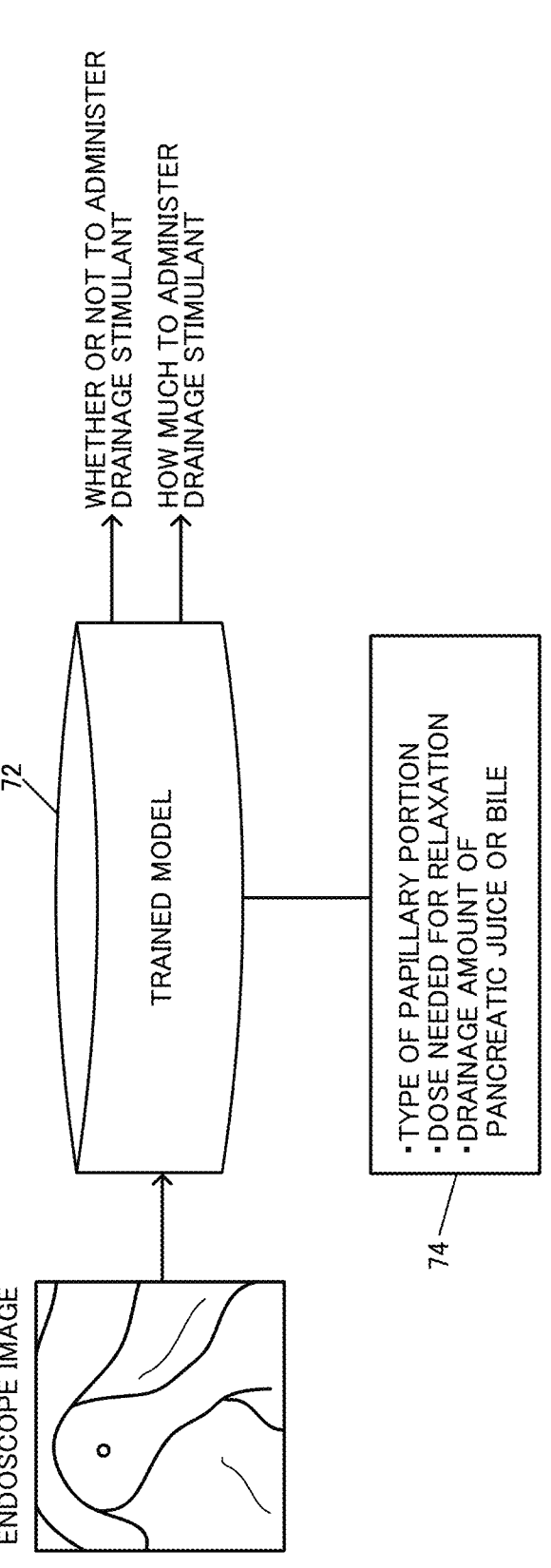
FIG. 18 explains another process using the trained model.

FIG. 18 illustrates another example process of the present embodiment using the trained model 72. The trained model 72 in FIG. 18 is trained also using information about the type of the papillary portion, for example, trained with the training data 74 based on information about the type of the papillary portion of each patient. For example, the trained model 72 learns a relation between the type of the papillary portion, the dose of the drainage stimulant needed to relax the papillary portion, and the drainage amount of pancreatic juice or bile. For example, the type of the papillary portion is from the class including common channel, separate, onion, and septal types in FIG. 4, or from the class including separate opening, onion, nodular, villous, flat, and vertically elongated types. For example, for patients with the papillary portion of a type that is initially relaxed to some extent, the trained model 72 is trained to determine that the papillary portion is relaxed upon detecting a small value of drainage amount of bile or pancreatic juice. On the other hand, for patients with the papillary portion of a type that is initially tight, the trained model 72 is trained to determine that the papillary portion is relaxed upon detecting a large value of drainage amount of bile or pancreatic juice. This allows the trained model 72 to output information about whether or not or how much to administer the drainage stimulant, in which individual patient differences according to the type of papillary portion are reflected.

Control of Endoscopic Operation by Electrical Driving

Figure 19:
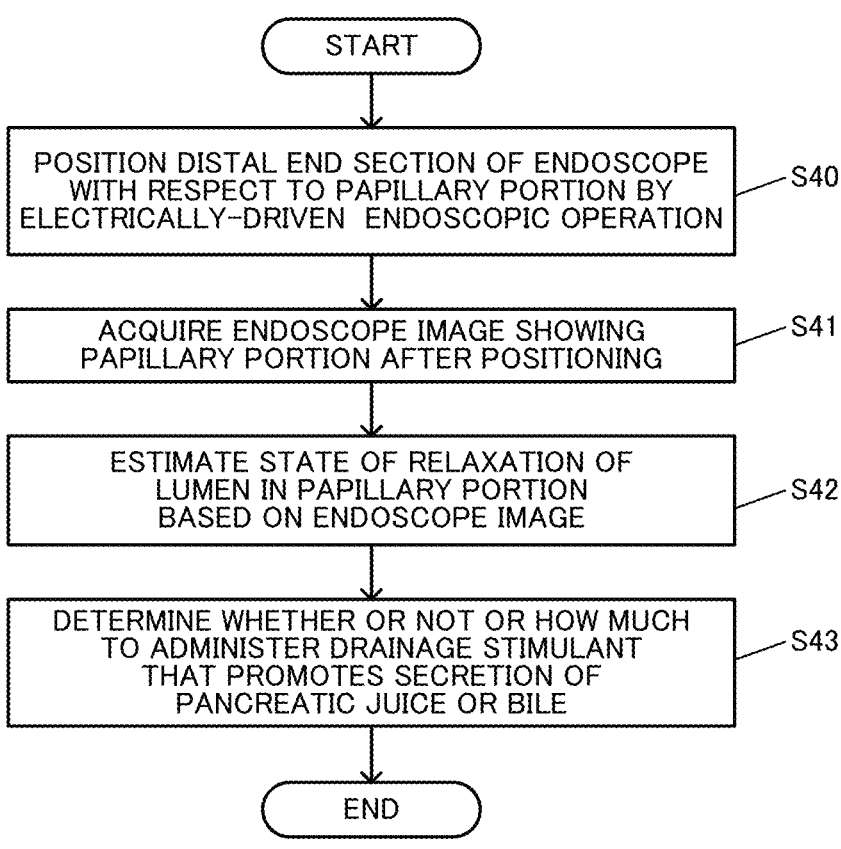
FIG. 19 is a flowchart explaining a process of the present embodiment when electrically-driven endoscopic operation is used.

As described with reference to FIG. 21 below, the endoscope 100 employed in the present embodiment is an endoscope whose endoscopic operation is electrically driven, where the endoscopic operation is at least one of forward and backward movement of the insertion section, a curving angle of the bending section of the insertion section, or rolling rotation of the insertion section. The processor 30 positions the insertion section of the endoscope 100 with respect to the papillary portion by the electrically-driven endoscopic operation, prior to administration of the drainage stimulant. In this case, the control section 50 performs the positioning of the distal end section of the endoscope 100 by the electrically-driven endoscopic operation. FIG. 19 is a flowchart explaining a process of the present embodiment when such electrically-driven endoscopic operation is performed.

First, the processor 30 (the control section 50; the same applies below) positions the distal end section of the endoscope 100 with respect to the papillary portion by the electrically-driven endoscopic operation (step S40). For example, as shown in FIG. 3, the distal end section of the endoscope 100 is positioned such that the endoscope image is captured at a predetermined angle of view and in a predetermined imaging direction. For example, a reference image for positioning may be prepared, a similarity between the endoscope image and the reference image may be determined, and the distal end section of the endoscope 100 may be positioned such that the endoscope image matches the reference image as closely as possible. Details of this positioning are described below. After positioning the distal end section of the endoscope 100, the processor 30 (the processing section 40) acquires an endoscope image showing the papillary portion (step S41). That is, the processor 30 acquires the endoscope image via the endoscope interface 62. Then, the processor 30 estimates a state of relaxation of the lumen in the papillary portion based on the endoscope image (step S42). The processor 30 then determines whether or not or how much to administer the drainage stimulant that promotes the secretion of pancreatic juice or bile (step S43). For example, as mentioned above, the processor 30 uses the trained model 72 to determine whether or not or how much to administer the drainage stimulant.

Thus, in FIG. 19, based on the endoscope image acquired after positioning the distal end section of the endoscope 100 by the electrically-driven endoscopic operation, a state of relaxation of the lumen in the papillary portion is estimated and whether or not or how much to administer the drainage stimulant is determined. Using the endoscope image positioned by electrical driving in this manner helps facilitate the process of estimating a state of relaxation based on the endoscope image and determining whether or not or how much to administer the drainage stimulant and helps improve the accuracy of this process. If, for example, endoscope images taken with various angles of view and in various imaging directions are input to the trained model 72 during the process of estimating a state of relaxation and determining whether or not or how much to administer the drainage stimulant, the accuracy of the process would decrease. In addition, in order for the trained model 72 to be able to estimate a state of relaxation and determine whether or not or how much to administer the drainage stimulant for endoscope images taken with various angles of view and in various imaging directions, a huge number of training endoscope images would be required during the training process. In this respect, in FIG. 19, the process of estimating a state of relaxation and determining whether or not or how much to administer the drainage stimulant is performed based on the endoscope image positioned by the electrically-driven endoscopic operation, so that the above problems can be prevented from occurring.

Figure 20:
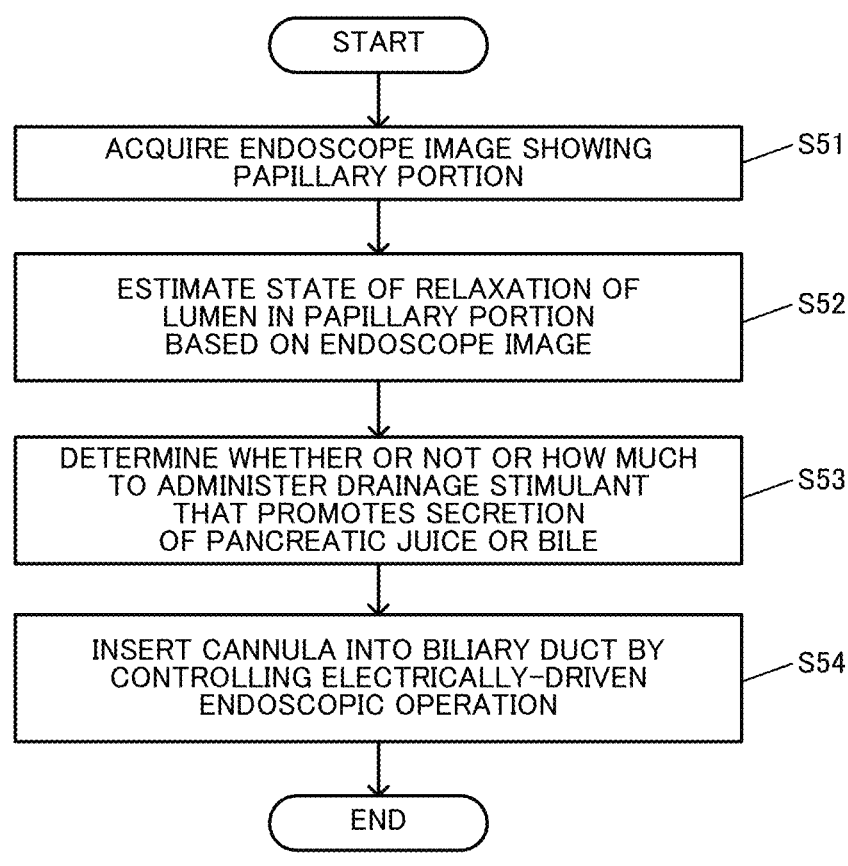
FIG. 20 is a flowchart explaining a process of the present embodiment when electrically-driven endoscopic operation is used.

Additionally, in the present embodiment, in the case of using the endoscope 100 whose endoscopic operation, which is at least one of forward and backward movement of the insertion section, a curving angle of the bending section of the insertion section, or rolling rotation of the insertion section, is electrically driven, the processor 30 (the control section 50) inserts the cannula into the biliary duct by controlling the electrically-driven endoscopic operation after administration of the drainage stimulant to the papillary portion. In this case, the control section 50 controls the electrically-driven endoscopic operation during insertion of the cannula into the biliary duct. FIG. 20 is a flowchart explaining a process of the present embodiment when such electrically-driven endoscopic operation is performed.

Steps S51, S52, S53 in FIG. 20 are similar to steps S21, S22, S23 of FIG. 12, so that descriptions thereof will be omitted. It should be noted that prior to step S51 of FIG. 20, the distal end section of the endoscope may be positioned by the electrically-driven endoscopic operation as in step S40 of FIG. 19, and an endoscope image showing the papillary portion may be acquired after the positioning. In FIG. 20, after step S53, the processor 30 (the control section 50) inserts the cannula into the biliary duct by controlling the electrically-driven endoscopic operation (step S54). That is, the processor 30 controls the electrically-driven endoscopic operation such that the cannula is inserted along the biliary duct by electrical driving of the endoscopic operation, which is at least one of forward and backward movement of the insertion section of the endoscope 100, a curving angle of the bending section of the insertion section, or rolling rotation of the insertion section.

In this way, the cannula can be inserted into the biliary duct by controlling the electrically-driven endoscopic operation after the lumen in the papillary portion has been relaxed by the drainage stimulant. For example, without administration of the drainage stimulant, the opening of the papillary portion would be closed, making it difficult to cannulate the opening with the cannula and insert it along the biliary duct. In this regard, in the present embodiment, the secretion of pancreatic juice or bile is promoted by administration of the drainage stimulant, and after the region near the opening has been relaxed, the cannula is inserted by the electrically-driven endoscopic operation. Specifically, the cannula is inserted by the electrically-driven endoscopic operation after the papillary portion has been so relaxed that administration of the drainage stimulant will no longer be needed, or after the dose of the drainage stimulant that can sufficiently relax the papillary portion has been administered. Thus, the cannula can be more easily inserted into the opening of the papillary portion by the electrically-driven endoscopic operation. This makes it possible to properly assist inexperienced operators and the like in performing cannulation during the ERCP procedure.

As described with reference to FIG. 21 below, the medical system 10 of the present embodiment includes the information processing system 20 and the endoscope 100. The present embodiment may be implemented as a method of operating the medical system 10. The method of operating the medical system 10 is a method of operating the medical system 10 including the endoscope 100 which captures endoscope images and whose endoscopic operation is electrically driven, where the endoscopic operation is at least one of forward and backward movement of the insertion section, a curving angle of the bending section of the insertion section, or rolling rotation of the insertion section. The operating method includes a step of positioning the insertion section with respect to the papillary portion of the duodenum by electrically-driven endoscopic operation, and a step of estimating a state of relaxation of the lumen in the papillary portion based on an endoscope image from the endoscope 100 whose insertion section has been positioned and determining whether or not or how much to administer the drainage stimulant that promotes the secretion of pancreatic juice or bile.

Medical System

A medical system of the present embodiment is now described. When cannulation into the biliary duct is performed, it is performed by referring to an endoscope image showing the papillary portion. As described with reference to FIGS. 3 and 4, there are various forms of papillary portion and luminal tissue, and it is difficult to specify the insertion position and insertion direction of the cannula from the endoscope image.

On the other hand, the operator estimates the position of the opening and the travelling direction of the biliary duct based on past cases, experiences, and the like while viewing the endoscope image, and tries to insert the cannula from the opening into the biliary duct according to the estimation. At this time, in order to more accurately estimate the position of the opening and the travelling direction of the biliary duct, it is desirable that the position of the papillary portion in the image and the angle of view of the image are easy to compare with those in the past cases or are familiar to the operator.

As shown in FIG. 1, such positioning of the endoscope is performed by operating the distal end of the endoscope insertion section reaching the duodenum from outside the body. However, since the insertion section and the organ through which the insertion section passes are flexible, the operation performed at the base end of the insertion section is not easily transmitted to the distal end section. In addition, since the distal end section of the endoscope is not fixed to the duodenum and floats in the air, the distal end section of the endoscope is not stable with respect to the papillary portion, and the positional relationship between the distal end section and the papillary portion is not easily determined. For these reasons, it is difficult to adjust the position of the distal end section of the endoscope so that the field of view of the endoscope is facing directly front of the papillary portion or so that the papillary portion appears in the center of the field of view.

Therefore, in the present embodiment, the above-described positioning is automated by an electric medical system to assist the ERCP procedure. Further, by adding a configuration in which the insertion section of the endoscope is held in the duodenum, the electrically-driven force can be easily transmitted to the distal end section of the endoscope and the position of the distal end section can be desirably controlled. The details of this structure are described below.

Figure 21:
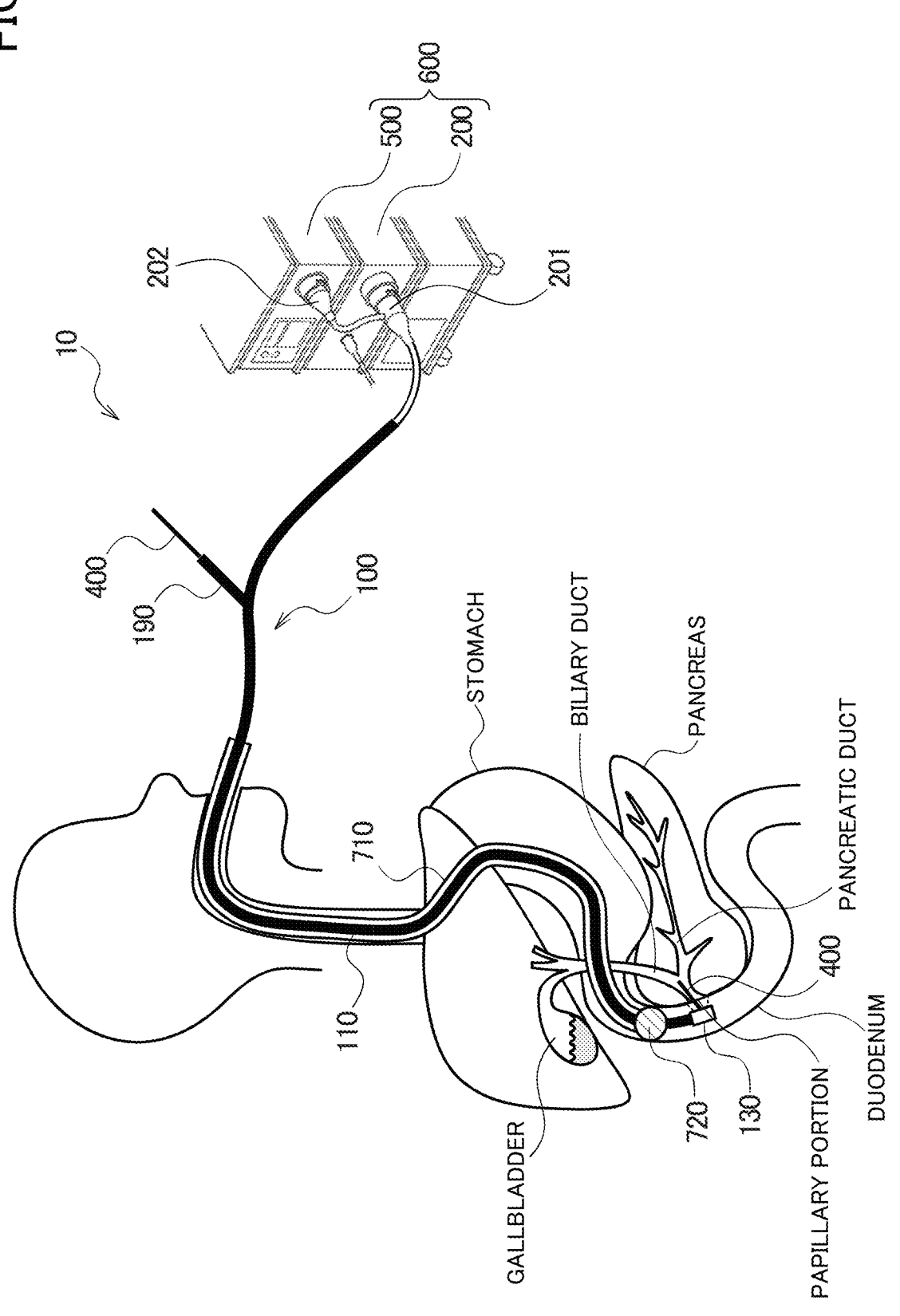
FIG. 21 shows a configuration example of a medical system of the present embodiment.

FIG. 21 shows a configuration example of a medical system 10 according to the present embodiment. The medical system 10 includes an endoscope 100 and a control device 600. Further, the medical system 10 may include an overtube 710, a balloon 720, and a treatment tool 400. The medical system 10 is also referred to as an endoscope system or an electric endoscope system. The information processing system 20 described with reference to FIG. 11 can be implemented by, for example, the hardware of the control device 600 in FIG. 21. Thus, the medical system 10 of the present embodiment includes the information processing system 20 implemented by the control device 600 and the endoscope 100.

The overtube 710 is a tube with a variable hardness that covers the insertion section 110 of the endoscope 100. The balloon 720 is provided near the distal end on the outer side of the overtube 710. When the endoscope 100 and the overtube 710 are inserted into the body, at least the bending section of the insertion section 110 is exposed from the distal end of the overtube 710. The bending section refers to a section structured to be bent at an angle corresponding to the curving operation in the vicinity of the distal end of the insertion section 110. The base end of the overtube 710 is present outside the body. The base end side of the insertion section 110 is exposed from the base end of the overtube 710.

An insertion opening 190 of the treatment tool is provided at the base end side of the insertion section 110, and a treatment tool channel for allowing the treatment tool 400 to pass through from the insertion opening 190 to the opening of the distal end section 130 is provided inside the insertion section 110. The insertion opening 190 of the treatment tool is also called a forceps opening; however, the treatment tool to be used is not limited to forceps.

The endoscope 100 is detachably connected to a control device 600 using connectors 201 and 202. The control device 600 includes a drive control device 200 to which the connector 201 is connected, and a video control device 500 to which the connector 202 is connected. The drive control device 200 controls the electrical driving of the endoscope 100 via the connector 201. Although not shown in FIG. 21, an operation device for manually operating the electrical driving may be connected to the drive control device 200. The video control device 500 receives an image signal from a camera provided at the distal end section 130 of the endoscope 100 via the connector 202, generates a display image from the image signal, and displays it on a display device (not shown). In FIG. 21, the drive control device 200 and the video control device 500 are shown as separate devices, but they may be structured as a single device. In this case, the connectors 201 and 202 may be integrated into a single connector.

Figure 22:
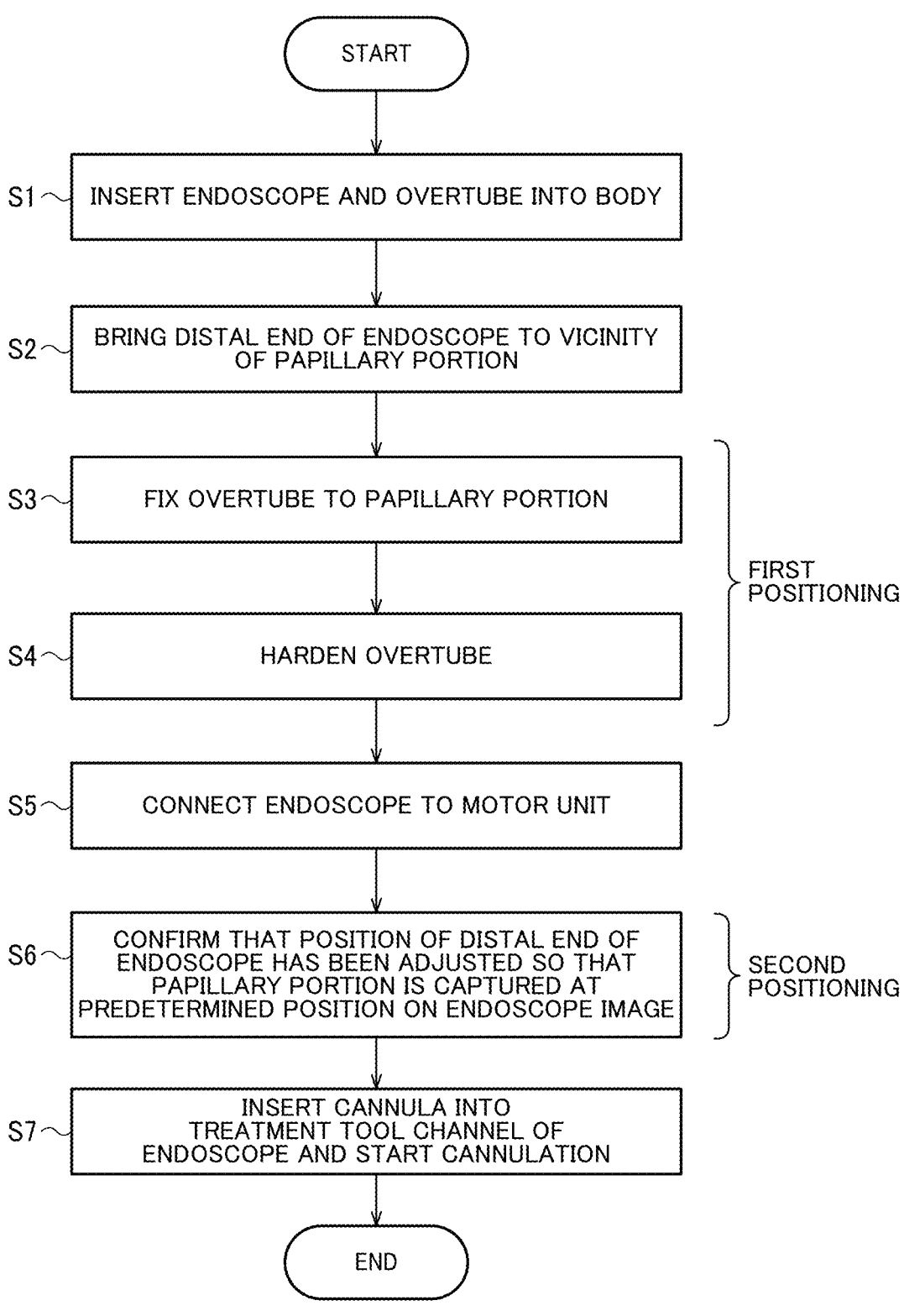
FIG. 22 is a flowchart of a procedure in the present embodiment.

FIG. 22 is a flowchart of the procedure in the present embodiment. Here, an electric endoscope is assumed in which the forward and backward movement of the insertion section 110 of the endoscope 100, the curving of the bending section of the insertion section 110, and the rolling rotation of the insertion section 110 are electrically driven. However, it is sufficient that at least one of these functions is electrically driven. The term "electrical driving" means that the endoscope is driven by a motor or the like based on an electrical signal for controlling the endoscopic operation. For example, when the electrical driving is manually operated, an operation input to the operation device is converted into an electrical signal, and the endoscope is driven based on the electrical signal. In the following, the forward and backward movement may be simply referred to as "forward/backward movement".

In step S1, the operator inserts the insertion section 110 of the endoscope 100 and the overtube 710 into the duodenum. More specifically, in a state where the insertion section 110 is inserted into the overtube 710, the insertion section 110 and the overtube 710 are inserted into the duodenum together. The overtube 710, which is changeable in hardness, is soft in step S1. For example, the operator can move the insertion section 110 and the overtube 710 forward by a non-electrically-driven manual operation so that they are inserted into the body. The non-electrical driving means that the endoscope 100 is not electrically driven by a motor or the like, instead, the force applied to the operation section is directly transmitted to the endoscope by a wire or the like, thereby operating the endoscope. For example, in the present embodiment, steps S1 to S4 are not electrically driven. In this case, it is sufficient that at least the forward/backward movement is not electrically driven, and the curving, the rolling rotation, or both may be manually operated by electrical driving.

In step S2, the operator inserts the insertion section 110 until the distal end section 130 reaches the vicinity of the papillary portion. For example, when the operator manually inserts the insertion section 110 by non-electrical driving, the operator inserts the insertion section 110 until the papillary portion becomes visible in the endoscope image. At this point, the distal end of the endoscope 100 does not need to accurately reach the papillary portion; the distal end of the endoscope 100 may reach a position before the papillary portion or past the papillary portion.

In step S3, the operator fixes the distal end of the overtube 710 to the duodenum. As an example, the operator performs an operation to inflate the balloon 720 provided near the distal end of the overtube 710, and fixes the distal end of the overtube 710 to the duodenum by the balloon 720. In step S4, the operator performs an operation to harden the overtube 710. At this time, the overtube 710 is hardened while maintaining its shape in a state immediately before hardening, that is, the shape when it is inserted from the mouth to the duodenum. As a result, the insertion section 110 is held by the hardened overtube 710 and the balloon 720, thereby fixing the insertion route of the insertion section 110. These steps S3 and S4 are referred to as first positioning.

In step S5, the endoscope 100 is connected to the motor unit, and the non-electrical driving is switched to the electrical driving. The method of switching between the non-electrical driving and the electrical driving varies depending on the configuration of the drive mechanism. For example, in steps S1 to S4, the forward/backward movement may be non-electrically driven and the curving and the rolling rotation may be electrically driven. In this case, the forward/backward movement may be switched from the non-electrical driving to the electrical driving by connecting the endoscope 100 to the forward/backward drive device (not shown). Further, when the curving operation by non-electrical driving is enabled by providing a curving operation dial or the like capable of non-electrically performing the curving operation, the curving movement may be switched from the non-electrical driving to the electrical driving, for example, by connecting the connector 201 to the drive control device 200. Alternatively, even if the motor unit is kept connected, the motor may be structured to be detachable by a clutch mechanism or the like, and the non-electrical driving may be switched to the electrical driving by the clutch mechanism. Step S5 may be performed before step S1. For example, when the forward/backward movement is manually operated by electrical driving, the endoscope 100 may be connected to the motor unit before step S1.

In step S6, the drive control device 200 automatically positions the distal end section 130 at the papillary portion, and the operator confirms that the position of the distal end section 130 has been adjusted so that the papillary portion is captured at a predetermined position on the endoscope image. The drive control device 200 acquires an endoscope image from the video control device 500 and performs positioning of the distal end section 130 of the endoscope 100 based on the endoscope image. More specifically, the drive control device 200 controls the forward/backward movement, curving, or rolling rotation by electrical driving so that the papillary portion is captured at a position registered in advance on the endoscope image. The position registered in advance is, for example, the center of the image. The positioning may be performed so that the opening of the luminal tissue is captured at a position registered in advance. Further, the drive control device 200 may perform electrical driving control based on the endoscope image so that the camera directly faces the front of the papillary portion or so that the papillary portion is captured at an appropriate angle of view. The drive control device 200 may also adjust the angle of view in imaging the papillary portion by controlling the diameter of the balloon 720 by electrical driving based on the endoscope image so that the distance between the camera and the papillary portion can be changed without changing the line-of-sight direction of the camera. This step S6 is referred to as second positioning.

In step S7, the operator inserts a cannula into the treatment tool channel through the insertion opening 190 to start cannulation into the biliary duct.

In FIG. 22, although the operation of the balloon in step S3 and the hardening of the overtube in step S4 are performed by non-electrical driving, they may be performed by electrical driving. In this case, the operator inputs an instruction from the operation device, and the drive control device 200 may inflate the balloon or harden the overtube by electrical driving using the instruction as a trigger. Alternatively, the drive control device 200 may perform an image recognition process for detecting the papillary portion from the endoscope image, and may automatically inflate the balloon or harden the overtube using the detection of the papillary portion from the endoscope image as a trigger.

According to the procedure flow described above, by inflating the balloon 720 before hardening the overtube 710 in step S3, the position of the distal end of the overtube 710 does not shift when the overtube 710 is hardened. Specifically, the distal end of the overtube 710 can be accurately positioned. In addition, by the first positioning in steps S3 and S4, the insertion route of the insertion section 110 is held by the balloon 720 and the overtube 710. As a result, in the second positioning in step S6, the forward/backward movement, curving, or rolling rotation of the endoscope 100 due to the electrical driving is easily transmitted from the base end side to the distal end of the insertion section 110.

Figure 23:
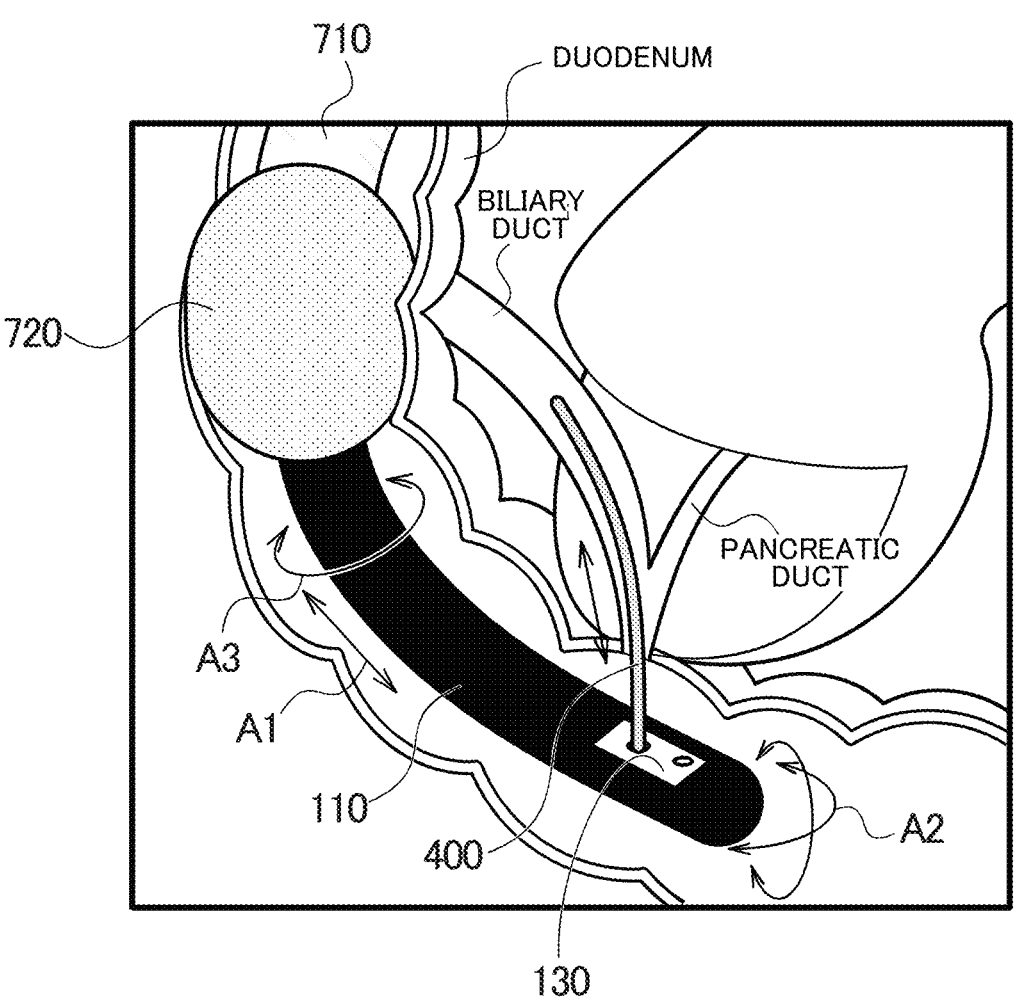
FIG. 23 shows the vicinity of the distal end of an endoscope positioned by an overtube and a balloon.

FIG. 23 shows the vicinity of the distal end of an endoscope positioned by the overtube 710 and the balloon 720. As shown in FIG. 23, the balloon 720 is fixed at a position slightly apart from the papillary portion to the pyloric side of the stomach. More specifically, the balloon 720 is positioned closer to the base end of the insertion section 110 than the base end of the bending section of the insertion section 110. By combining such a balloon 720 with the overtube 710 having a variable hardness, the bending section exposed to the papillary portion side from the balloon 720 and the distal end section 130 can be freely operated without being fixed, and the electrical driving from the base end side can be efficiently transmitted to the distal end section 130 of the endoscope.

The endoscopic operation by the electrical driving is the forward and backward movement shown in A1, a curving movement shown in A2, or a rolling rotation shown in A3. The forward movement is a shift toward the distal end side along the axial direction of the insertion section 110, and the backward movement is a shift toward the base end side along the axial direction of the insertion section 110. The curving movement is a movement by which the angle of the distal end section 130 is changed due to the bending of the bending section. The curving movement includes curving movements in two orthogonal directions, which can be controlled independently. One of the two orthogonal directions is referred to as the vertical direction and the other is referred to as the horizontal direction. The rolling rotation is a rotation about an axis of the insertion section 110.

FIG. 23 shows an example in which the balloon 720 is attached to the distal end of the overtube 710 and the endoscope protrudes from the distal end of the overtube 710. However, it is sufficient that the overtube 710 and the balloon 720 are configured so that a portion of the bending section beyond the base end can freely move. For example, it may also be arranged such that a soft tube with a constant hardness extends beyond the overtube with a variable hardness, and the balloon 720 is attached to the boundary thereof. In this case, although a part of the base end side of the bending section is covered with the soft tube, its movement is not hindered.

Figure 24:
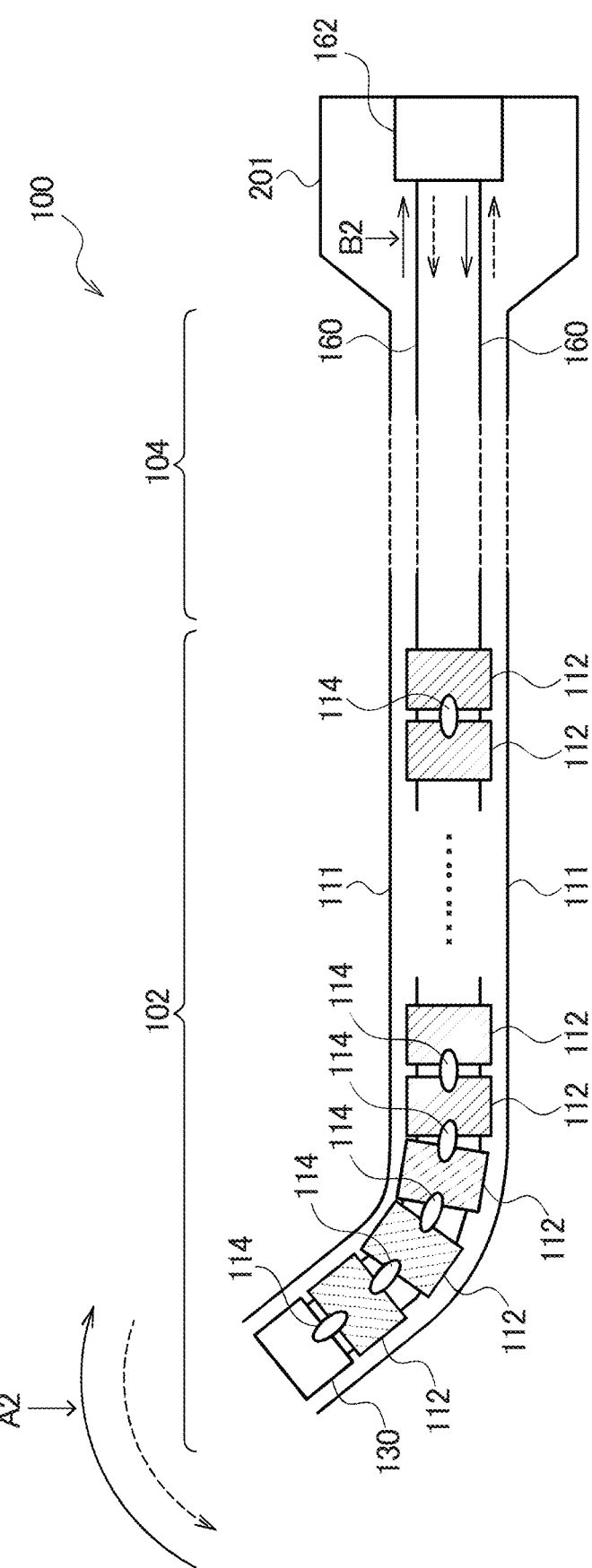
FIG. 24 is a schematic view of an endoscope including a bending section and a driving mechanism thereof.

FIG. 24 is a schematic view of an endoscope 100 including a bending section 102 and a driving mechanism thereof. An endoscope 100 includes a bending section 102, a soft section 104, and a connector 201.

The bending section 102 and the soft section 104 are covered with an outer sheath 111. The bending section 102 includes a plurality of curving pieces 112 and a distal end section 130 connected to the distal end of the curving pieces 112. Each of the plurality of curving pieces 112 and the distal end section 130 is connected in series from the base end side to the distal end side by a rotatable connecting section 114, thereby forming a multi joint structure. The connector 201 is provided with a coupling mechanism 162 on the endoscope side connected to a coupling mechanism on the drive control device 200 side. By attaching the connector 201 to the drive control device 200, it is possible to electrically drive the curving movement. A curving wire 160 is provided in the outer sheath 111. One end of the curving wire 160 is connected to the distal end section 130. The curving wire 160 passes through the soft section 104 by penetrating through a plurality of curving pieces 112, turns back in a coupling mechanism 162, passes through the soft section 104 again, penetrates through the plurality of curving pieces 112. The other end of the curving wire 160 is connected to the distal end section 130. The driving force from the wire drive section of the drive control device 200 is transmitted to the curving wire 160 via the coupling mechanism 162 as the pulling force of the curving wire 160.

As shown by the solid line arrow B2 in FIG. 24, when the upper wire in the figure is pulled, the lower wire is pushed, whereby the multiple joints of the curving pieces 112 are bent upward in the figure. As a result, as indicated by the solid line arrow A2, the bending section 102 is curved upward in the figure. When the lower wire in the figure is pulled as indicated by the dotted arrow B2, similarly, the bending section 102 is curved downward in the figure as indicated by the dotted arrow A2. As described with reference to FIG. 23, the bending section 102 can be curved independently in two orthogonal directions. Although FIG. 24 shows a curving mechanism for one direction, two sets of curving wires are actually provided, and each curving wire can be curved independently in two directions by being pulled independently by the coupling mechanism 162.

Note that the mechanism for the electrically-driven curving is not limited to that described above. For example, a motor unit may be provided instead of the coupling mechanism 162. Specifically, it may be arranged such that the drive control device 200 transmits a control signal to the motor unit via the connector 201, and the motor unit drives the curving movement by pulling or relaxing the curving wire 160 based on the control signal.

Figure 25:
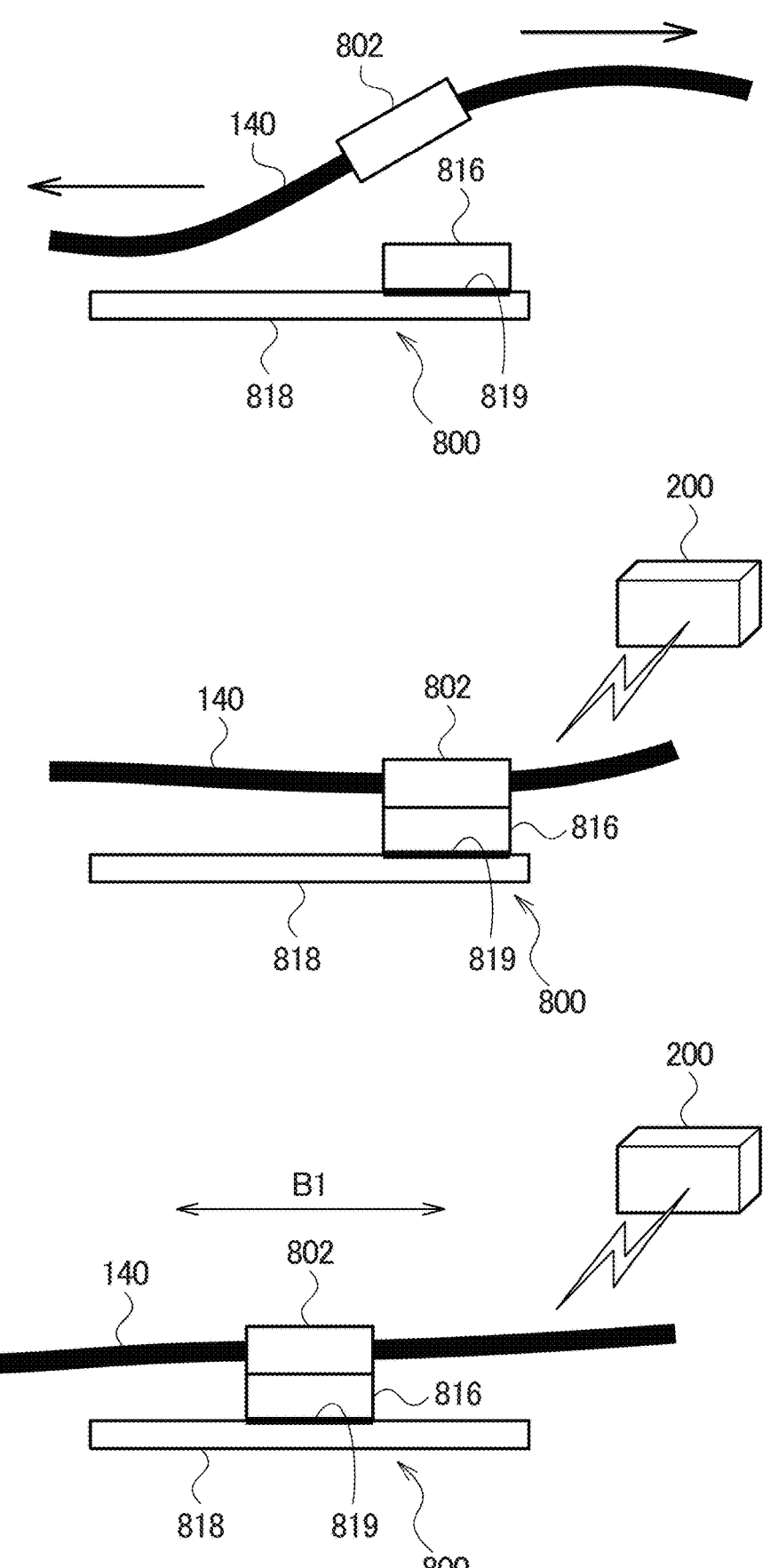
FIG. 25 shows a detailed configuration example of a forward/backward drive device.

FIG. 25 shows a detailed configuration example of a forward/backward drive device 800. The forward/backward drive device 800 includes a motor unit 816, a base 818, and a slider 819.

As shown in the upper and middle figures, the extracorporeal soft section 140 of the endoscope 100 is provided with an attachment 802 detachable from the motor unit 816. As shown in the middle figure, the attachment of the attachment 802 to the motor unit 816 enables electrical driving of forward/backward movement. As shown in the lower figure, the slider 819 supports the motor unit 816 while enabling the motor unit 816 to move linearly with respect to the base 818. The slider 819 is fixed to an operating table. As shown in B1, the drive control device 200 transmits a forward or backward control signal to the motor unit 816 by wireless communication, and the motor unit 816 and the attachment 802 move linearly on the slider 819 based on the control signal. As a result, the forward and backward movement of the endoscope 100 shown in A1 in FIG. 23 is achieved. Note that the drive control device 200 and the motor unit 816 may be connected by wired connection.

Figure 26:
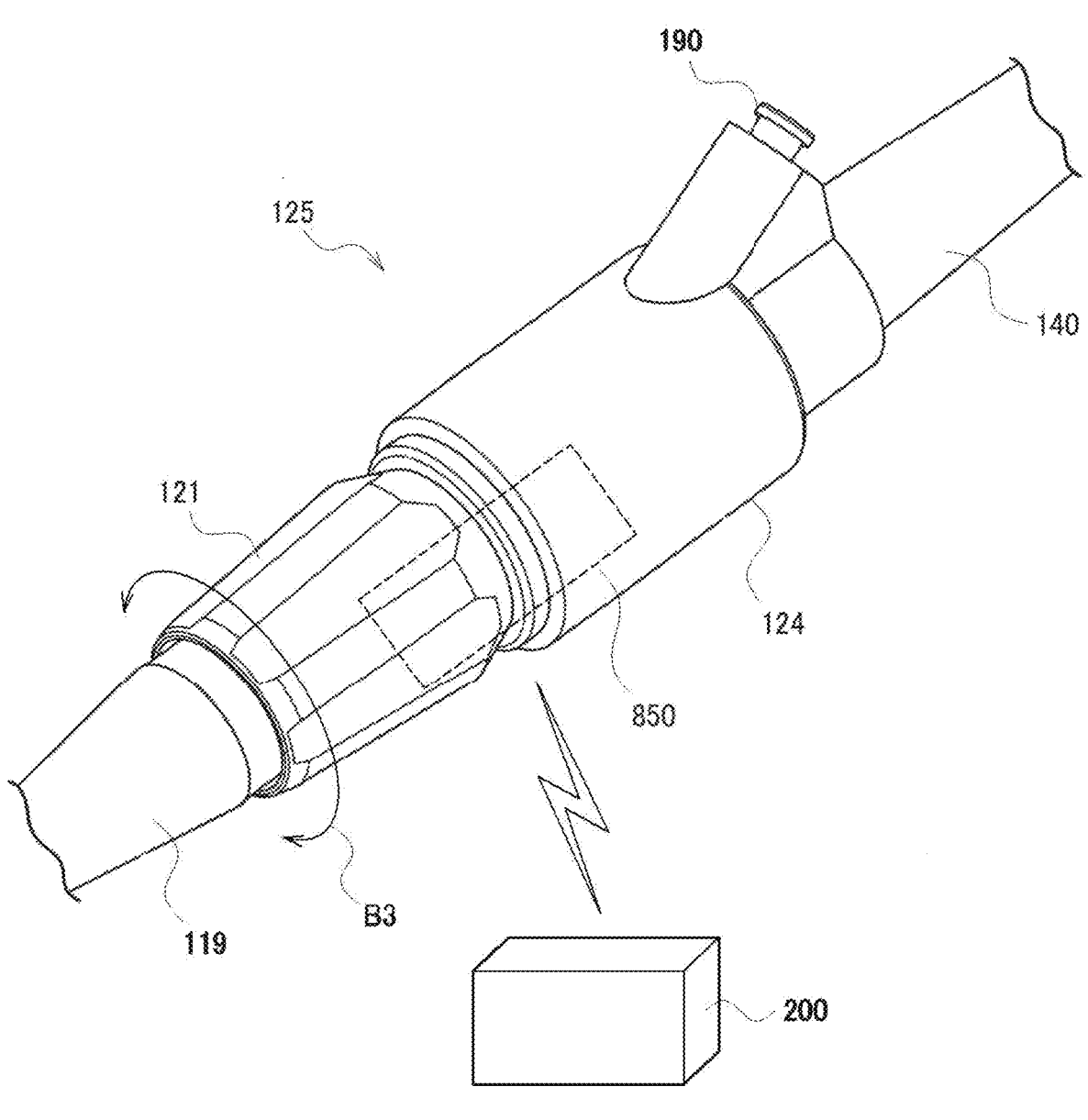
FIG. 26 is a perspective view of a connecting section including a rolling drive device.

FIG. 26 is a perspective view of the connecting section 125 including a rolling drive device 850. The connecting section 125 includes a connecting section main body 124 and a rolling drive device 850.

The insertion opening 190 of the treatment tool is provided in the connecting section main body 124 and is connected to the treatment tool channel inside the connecting section main body 124. The connecting section main body 124 has a cylindrical shape, and a cylindrical member coaxial with the cylinder is rotatably provided inside the connecting section main body 124. The base end section of the intracorporeal soft section 119 is fixed to the outside of the cylindrical member, and the base end section serves as a rolling operation section 121. As a result, the intracorporeal soft section 119 and the cylindrical member can rotate with respect to the connecting section main body 124 about the axial direction of the intracorporeal soft section 119. The rolling drive device 850 is a motor unit provided inside the connecting section main body 124. As shown in B3, the drive control device 200 transmits a rolling rotation control signal to the rolling drive device 850 by wireless communication, and the rolling drive device 850 rotates the base end section of the intracorporeal soft section 119 with respect to the connecting section main body 124 based on the control signal, thereby causing rolling rotation of the intracorporeal soft section 119. As a result, the rolling rotation of the endoscope 100 shown in A3 in FIG. 23 is achieved. The rolling drive device 850 may include a clutch mechanism, and the rolling rotation may be switched between non-electrical driving and electrical driving by the clutch mechanism. The drive control device 200 and the rolling drive device 850 may be connected by wired connection via a signal line passing through the internal route 101.

Figure 27:
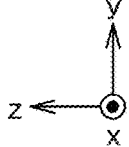
FIG. 27 shows a detailed configuration example of a distal end section of an endoscope including a raising base of a treatment tool.

FIG. 27 shows a detailed configuration example of a distal end section 130 of an endoscope including a raising base of a treatment tool. The upper figure shows an external view of the distal end section 130. An opening 131 of a treatment tool channel, a camera 132, and an illumination lens 133 are provided on the side surface of the distal end section 130. As shown in the lower figure, the direction parallel to the axial direction of the distal end section 130 is defined as z direction, the direction parallel to the line-of-sight direction of the camera 132 is defined as y direction, and the direction orthogonal to the z direction and they direction is defined as x direction. The lower figure shows a cross-sectional view of the distal end section 130 in a plane that is parallel to the yz plane of the treatment tool channel and that passes through the opening 131 of the treatment tool channel.

The distal end section 130 includes a raising base 134 and a raising base wire 135. The raising base 134 is swingable about an axis parallel to the x direction. One end of the raising base wire 135 is connected to the raising base 134, while the other end is connected to the drive control device 200 via the connector 201. As shown in B4, the wire drive section of the drive control device 200 pushes and pulls the raising base wire 135 to swing the raising base 134, thereby, as shown in A4, changing the raising angle of the treatment tool 400. The raising angle is an angle of the treatment tool 400 protruding from the opening 131. The raising angle can be defined, for example, by an angle formed by the treatment tool 400 protruding from the opening 131 and the z direction.

Although the embodiments to which the present disclosure is applied and the modifications thereof have been described above, the present disclosure is not limited to the embodiments and the modifications thereof, and various modifications and variations in elements may be made in implementation without departing from the spirit and scope of the present disclosure. The plurality of elements disclosed in the embodiments and the modifications described above may be combined as appropriate to form various disclosures. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term (the processor) cited with a different term (the processing section or the control section) having a broader meaning or the same meaning at least once in the specification and the drawings can be replaced by the different term in any place in the specification and the drawings.

What is claimed is:

1. A cannulation method comprising:
   inserting an endoscope into a duodenum;
   bringing a distal end section of the endoscope to a position where a duodenal papilla is within a field of view of the endoscope;
   promoting secretion of one of pancreatic juice or bile by administering a drainage stimulant;
   determining an amount of relaxation of the duodenal papilla; and
   performing cannulation into a biliary duct through the duodenal papilla where the amount of relaxation is greater than a predetermined amount;
   wherein the promoting of the secretion comprises determining a dose of the drainage stimulant based on the determined amount of relaxation of the duodenal papilla; and
   the determination of the amount of relaxation of the duodenal papilla is based on:
   at least one of a luminance of the pancreatic juice, and a color of the pancreatic juice in an endoscope image acquired by the endoscope; or
   at least one of a luminance of the bile, and a color of the bile in the endoscope image acquired by the endoscope.

2. The cannulation method according to claim 1, wherein the promoting of the secretion comprises administering the drainage stimulant from the endoscope brought to the position.

3. The cannulation method according to claim 1, wherein the promoting of the secretion comprises administering the drainage stimulant from the endoscope to the duodenal papilla subsequent to the bringing of the distal end section of the endoscope to the position.

4. The cannulation method according to claim 1, wherein the promoting of the secretion comprises administering the drainage stimulant orally prior to the inserting of the endoscope.

5. The cannulation method according to claim 1, wherein the promoting of the secretion comprises administering the drainage stimulant as an agent for promoting secretion of pancreatic juice.

6. The cannulation method according to claim 1, wherein the promoting of the secretion comprises administering the drainage stimulant as an agent for promoting secretion of bile.

7. The cannulation method according to claim 1, subsequent to the bringing of the distal end section of the endoscope to the position where the duodenal papilla is within the field of view of the endoscope, fixing a position of the endoscope at the position.

8. The cannulation method according to claim 1, further comprising, subsequent to the bringing of the distal end section of the endoscope to the position where the duodenal papilla is within the field of view of the endoscope, at least indirectly increasing a hardness of the endoscope.

9. The cannulation method according to claim 1, wherein the bringing of the distal end section of the endoscope to the position where the duodenal papilla is within the field of view of the endoscope comprises electrically driving one or more of a forward/backward movement, rolling movement and curving movement of the endoscope in an electrically driving mode.

10. The cannulation method according to claim 9, further comprising switching between the electrically driving mode and a manually driving mode.

* * * * *